(12) United States Patent
Elsner et al.

(10) Patent No.: US 11,491,017 B2
(45) Date of Patent: Nov. 8, 2022

(54) FLOATING JOINT REPLACEMENT DEVICE WITH SUPPORTIVE SIDEWALL

(71) Applicant: Active Implants LLC, Memphis, TN (US)

(72) Inventors: Jonathan J. Elsner, Cambridge, MA (US); Eran Linder-Ganz, Tel Aviv (IL); Henry A. Klyce, San Francisco, CA (US)

(73) Assignee: Active Implants LLC, Memphis, TN (US)

( * ) Notice: Subject to any disclaimer, the term of this patent is extended or adjusted under 35 U.S.C. 154(b) by 0 days.

(21) Appl. No.: 16/047,689

(22) Filed: Jul. 27, 2018

(65) Prior Publication Data
US 2019/0029834 A1     Jan. 31, 2019

Related U.S. Application Data

(60) Provisional application No. 62/538,109, filed on Jul. 28, 2017.

(51) Int. Cl.
*A61F 2/38* (2006.01)
*A61F 2/30* (2006.01)

(52) U.S. Cl.
CPC ........ *A61F 2/3872* (2013.01); *A61F 2/30756* (2013.01); *A61F 2/3868* (2013.01);
(Continued)

(58) Field of Classification Search
CPC .. A61F 2/3872; A61F 2/30756; A61F 2/3868; A61F 2002/3895;
(Continued)

(56) References Cited

U.S. PATENT DOCUMENTS

| 4,207,627 A | 6/1980 | Cloutier |
| 4,795,468 A * | 1/1989 | Hodorek ............... A61F 2/389 |
| | | 623/20.28 |

(Continued)

FOREIGN PATENT DOCUMENTS

| CN | 101534750 A | 9/2009 |
| CN | 201438977 U | 4/2010 |

(Continued)

OTHER PUBLICATIONS

International Search Report and Written Oolnion received in Patent Coooeration Treaty Application No. PCT/US2018/044161, dated Oct. 16, 2018, 17 pages.
(Continued)

*Primary Examiner* — Brian A Dukert
*Assistant Examiner* — Rebecca Lynee Zimmerman
(74) *Attorney, Agent, or Firm* — Haynes and Boone, LLP

(57) ABSTRACT

A meniscus replacement device for replacing damaged soft tissue at a host knee includes a first component comprising a first tissue-interface surface shaped to free-floatingly interface with tissue structure of one of a femur and a tibia in a knee joint having a damaged soft tissue, and comprises a second component comprising a second tissue-interface surface shaped to free-floatingly interface with a second tissue structure of the other of the femur and the tibia in the knee joint. The second component may include a containment cavity receiving at least a portion of the first component. In another form, the free floating soft joint tissue replacement component and the base component are fixed together. In some aspects, the second tissue-interface surface is shaped to fit contours of a natural tibia plateau. In some aspects, the first tissue-interface surface is shaped to fit contours of a femoral surface.

28 Claims, 16 Drawing Sheets

(52) U.S. Cl.
CPC ... *A61F 2/3886* (2013.01); *A61F 2002/30014* (2013.01); *A61F 2002/30131* (2013.01); *A61F 2002/30133* (2013.01); *A61F 2002/30187* (2013.01); *A61F 2002/30535* (2013.01); *A61F 2002/30754* (2013.01); *A61F 2002/30766* (2013.01); *A61F 2002/3895* (2013.01); *A61L 2430/06* (2013.01)

(58) Field of Classification Search
CPC .... A61F 2002/3018; A61F 2002/30754; A61F 2002/30133; A61F 2002/30014; A61F 2/3886; A61F 2002/30131; A61F 2002/30535; A61F 2002/30766; A61F 2/38; A61L 2430/06
See application file for complete search history.

(56) References Cited

U.S. PATENT DOCUMENTS

| | | | |
|---|---|---|---|
| 5,879,387 | A | 3/1999 | Jones et al. |
| 5,964,808 | A | 10/1999 | Blaha et al. |
| 6,206,927 | B1 | 3/2001 | Fell et al. |
| 7,291,169 | B2 | 11/2007 | Hodorek |
| 2003/0055500 | A1* | 3/2003 | Fell ............... A61F 2/3868 623/14.12 |
| 2003/0114934 | A1 | 6/2003 | Steinberg |
| 2004/0024641 | A1 | 2/2004 | Cartwright |
| 2004/0199250 | A1 | 10/2004 | Fell |
| 2004/0247641 | A1 | 12/2004 | Felt et al. |
| 2005/0033424 | A1 | 2/2005 | Fell |
| 2005/0278025 | A1 | 12/2005 | Ku et al. |
| 2006/0235537 | A1* | 10/2006 | Kuczynski ........... A61F 2/38 623/20.3 |
| 2007/0067032 | A1 | 3/2007 | Felt et al. |
| 2007/0293947 | A1 | 12/2007 | Mansmann |
| 2012/0209396 | A1 | 8/2012 | Myung et al. |
| 2012/0232656 | A1 | 9/2012 | Gedet et al. |
| 2013/0023989 | A1* | 1/2013 | Fox ............... A61F 2/3872 623/14.12 |
| 2014/0296981 | A1 | 10/2014 | Linder-Ganz et al. |
| 2016/0206435 | A1 | 7/2016 | Nocco et al. |

FOREIGN PATENT DOCUMENTS

| | | |
|---|---|---|
| CN | 103415270 A | 11/2013 |
| EP | 1327424 A1 | 7/2003 |

OTHER PUBLICATIONS

Australian Patent Office, Examination Report, for Application No. 2018306724, dated May 25, 2020, 4 pages.
Canadian Patent Office, "Canadian Office Action" for Application No. 3,069,233, dated Feb. 22, 2021, 8 pages.
Chinese Patent Office, Chinese Office Action for Application No. 201880049264.2 dated Apr. 30, 2021 and English translation, 14 pages.
Canadian Patent Office,"Canadian Office Action", for Application No. 3,069,233, dated Aug. 4, 2021, 8 pages.
European Patent Office, "Extented European Search Report", Application No. 21174359.6, dated Jul. 9, 2021, 7 pages.
Canadian Patent Office, Office Action for Canadian Application No. 3,069,233, dated Feb. 9, 2022, 7 pages.
Office Action received in Canadian Application No. 3,069,233, dated Sep. 1, 2022, 3 pages.

* cited by examiner

FLOATING JOINT REPLACEMENT DEVICE WITH SUPPORTIVE SIDEWALL

PRIORITY DATA

This application claims priority to U.S. Provisional Patent Application Ser. No. 62/538,109, filed on Jul. 28, 2017, the entire disclosure of which is hereby incorporated herein by reference.

FIELD OF THE INVENTION

The disclosure generally relates to medical prosthetic devices and methods. More specifically, the disclosure relates to prosthetic devices that replace at least part of the functionality of the natural soft tissue, such as a meniscus or cartilage, at joint bearing surfaces.

BACKGROUND

A knee has two menisci, a lateral meniscus and a medial meniscus. Each meniscus is a crescent-shaped fibrocartilaginous tissue attached to the tibia at an anterior and a posterior horn. Damage to the meniscus can cause pain and arthritis. Further, damage to cartilage on the bearing surfaces of the tibia and femur may lead to additional pain and may cause additional damage to the meniscus and/or other tissues. Accordingly, current practices for treating patients with damaged knee cartilage are to perform a total knee replacement. Alternatively, if the damaged cartilage is limited to one side of the knee (e.g., only medial or lateral compartment), a unicompartmental knee replacement procedure may be performed where the femur and tibia bones are milled off and implants are inserted into both bones to perform the bearing function of the knee. In such a procedure, even though cartilage of only one of the bone surfaces is damaged, both cartilage surfaces will be removed and replaced with an artificial bearing surface. The total or unicompartmental knee replacement procedures are invasive and result in significant pain and rehabilitation time for the patient.

There remains a need for less traumatic and bone sparing devices that can accomplish load bearing and joint function through a range of joint motions. While existing devices, systems, and methods have attempted to address these issues, they have not been satisfactory in all respects. Accordingly, there is a need for the improved devices and methods described herein in accordance with the disclosure.

SUMMARY

In some implementations, this disclosure is directed to a meniscus replacement device for replacing damaged soft tissue at a host knee. The device may include a first component comprising a first tissue-interface surface shaped to free-floatingly interface with tissue structure of one of a femur and a tibia in a knee joint having a damaged soft tissue. The device may also include a second component comprising a second tissue-interface surface shaped to free-floatingly interface with a second tissue structure of the other of the femur and the tibia in the knee joint. The second component may have a containment cavity receiving at least a portion of the first component therein to inhibit movement of the first component relative to the second component.

In some aspects, the second tissue-interface surface is shaped to fit contours of a natural tibia plateau, and the first tissue-interface surface is shaped to fit contours of a femoral surface. In some aspects, the first component is formed of a relatively more soft first material and the second component is formed of a relatively less soft second material that is shaped to receive and limit radial expansion of the first material. In some aspects, the second component comprises a locking structure that secures the first component in the containment cavity. In some aspects, the first component includes a bone-relief recess formed on the first tissue-interface surface. The bone-relief recess may be arranged to prevent load-bearing contact between the first component and a portion of bone structure of the knee.

In some implementations, this disclosure is directed to a disc-shaped joint replacement device for replacing damaged soft tissue at a host joint. The device may include a first component comprising a first tissue-interface surface shaped to free-floatingly interface with a first tissue structure of the joint. The first tissue-interface surface may include a concave shape arranged to receive the first tissue structure and may be formed of a relatively more soft material configured to partially deform under load of the first tissue structure of the joint. The device also may include a second component including a second tissue-interface surface shaped to free-floatingly interface with a second tissue structure of the joint opposing the first tissue structure. The second component may be formed of a relatively more rigid material and may include a containment cavity receiving at least a portion of the first component therein. The second component may be arranged to limit radial expansion of the first component under load. The first and second components together may have a disc-shape.

In some implementations, this disclosure is directed to a method of implanting a joint replacement device between a first bone structure and an adjacent second bone structure. The method may include introducing a first component into a cavity of a second component, engaging a locking mechanism that secures the first component within the cavity of the second component, and introducing the first and second components between opposing tissue surfaces at a joint having damaged soft tissue without removing or penetrating bone tissue at the joint. In some aspects, the method may include positioning the first and second components so that a first tissue interface surface receives a portion of the first bone structure and a second tissue interface surface receives a portion of the second bone structure.

In some aspects, the method includes selecting the first component from a plurality of first components each arranged to fit within a second free-floating component and each having a differently contoured first tissue interface surface. In some aspects, the method includes closing an incision without mechanically connecting the first or second components to the first or second bone structure. In some aspects, the method includes positioning the first and second component comprises manipulating the first component so that the first bone structure fits within contours of the first component and includes positioning the first and second components comprises manipulating the first component so that the second bone structure fits within contours of the second component. In some aspects, the method includes positioning a bone-relief recess area formed on the upper surface of the free floating soft joint tissue replacement component over a portion of the first bone structure to limit contact between the portion of the first bone structure and the prosthetic device.

BRIEF DESCRIPTION OF DRAWINGS

Other features and advantages of the disclosure will become apparent in the following detailed description of embodiments of the disclosure with reference to the accompanying of drawings.

DETAILED DESCRIPTION

Figure 1:
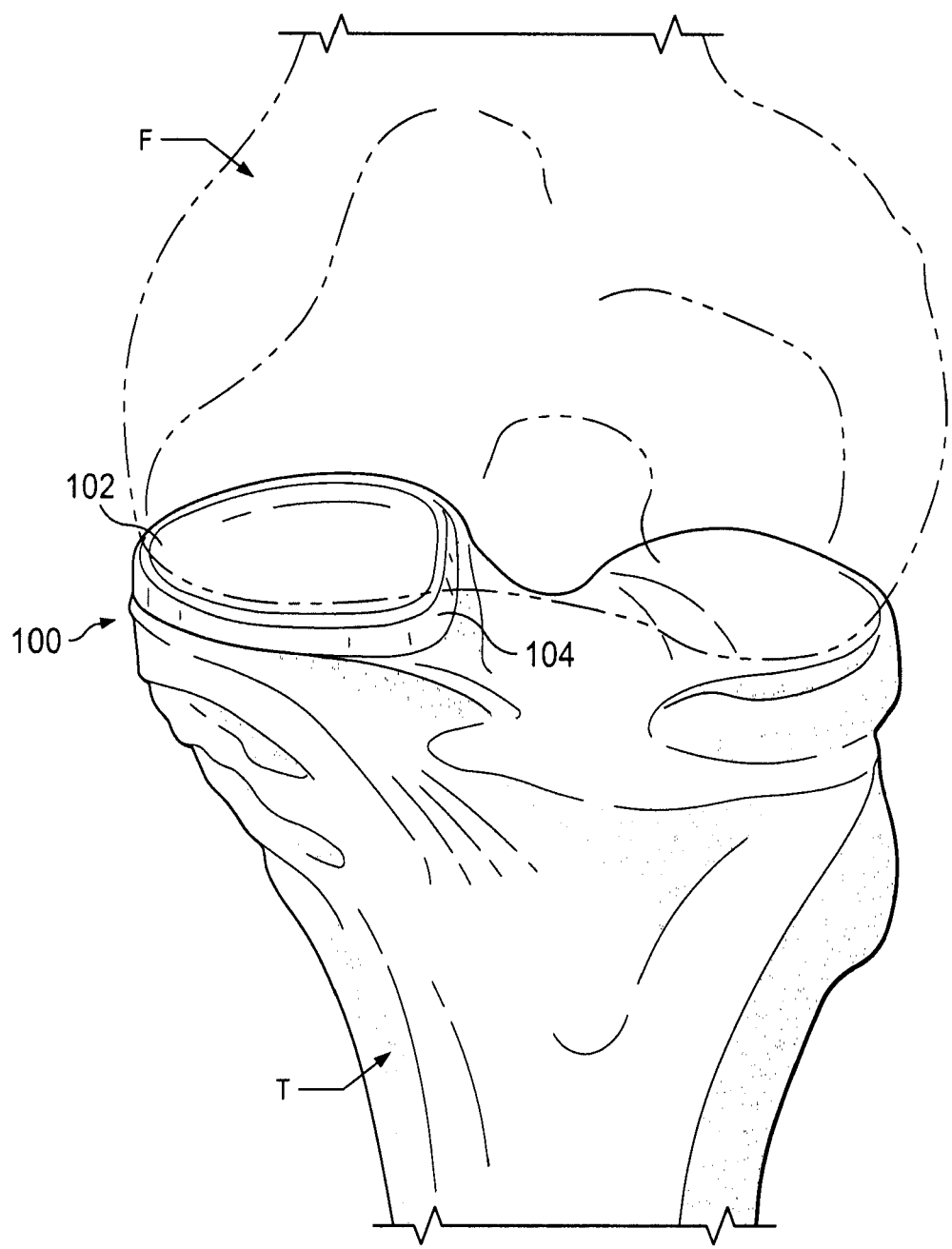
FIG. 1 is a diagrammatic view of a prosthetic meniscus device implanted in a left knee joint between femur F and tibia T, according to an exemplary implementation.

For the purposes of promoting an understanding of the principles of the disclosure, reference will now be made to the embodiments illustrated in the drawings, and specific language will be used to describe the illustrated embodiments. It is nevertheless understood that no limitation of the scope of the disclosure is intended. Any and all alterations or modifications to the described devices, instruments, and/or methods, as well as any further application of the principles of the disclosure that would be apparent to one skilled in the art are encompassed by the disclosure even if not explicitly discussed herein. Further, it is fully contemplated that the features, components, and/or steps described with respect to one embodiment may be combined with the features, components, and/or steps described with respect to other embodiments of the disclosure.

FIG. 1 is a diagrammatic view of a prosthetic meniscus device 100 (also referred to as a joint replacement device) implanted in a joint. The prosthetic meniscus device 100 may be used to replace tissue such as a meniscus or cartilage that may be found between adjacent bone structures in a joint. As used herein, bone structure on adjacent sides of a joint is typically not considered to be soft-tissue. In the example shown, the joint is a left knee joint and the prosthetic meniscus device 100 is disposed between femur F and tibia T. In this example, the prosthetic meniscus device 100 is implanted into the knee such that the prosthetic meniscus device floats inside the knee joint. As used herein, the term "float" means that the device is not anchored in the joint using a mechanical device structure, such as a screw, a fin, a pointed protrusion, or other structure that would penetrate the bone to secure the device in place or will connect the device to the capsule or other tissues. Because the prosthetic meniscus device 100 floats inside the knee joint, the implant may not cause, or may at least minimize, permanent damage to the patient's undamaged tibia or other bone and/or soft tissue structure(s) engaged by the prosthetic meniscus device 100 in some embodiments. In some instances, the prosthetic meniscus device 100 is implanted to alleviate the patient's knee problems while avoiding permanent destruction of the patient's anatomy, which may occur if traditional joint repair techniques are used, such as cutting or reaming a large opening in the tibia, femur or other hard and soft tissues. Because the surrounding bone structure may remain largely or completely intact, in some instances, the prosthetic meniscus device 100 may be subsequently removed and replaced with another prosthetic device or treatment without adversely affecting the subsequent treatment. While the prosthetic meniscus device 100 will be described herein primarily with reference to a knee joint meniscus device that may be disposed between a femur and tibia, other implementations of the prosthetic meniscus device are suitably shaped and sized for implantation in a shoulder joint, an ankle joint, a hip joint, or other joint in the human body.

In some implementations, the prosthetic meniscus device 100 replaces some or all of the function of a natural meniscus and is configured to interact with the opposing bone and/or cartilage surfaces to facilitate movement of a joint with a damaged meniscus. In the example of a knee joint, the prosthetic meniscus device 100 device may be disposed between tibia and femur surfaces to facilitate movement of a knee joint having a damaged meniscus. In some implementations, the prosthetic meniscus device 100 is inserted between tibia and femur surfaces of a knee joint and prevents further deterioration of the medial meniscus and/or cartilage and bone tissues. In another embodiment, prosthetic meniscus device 100 serves as a temporary implant that is in place while natural meniscus is treated or regrown with a biologic. In that regard, the prosthetic meniscus device 100 can be disposed between and in contact with a lateral femoral bearing surface or medial femoral condyle in the femur and the natural lateral tibial plateau in the tibia. In a further embodiment, the prosthetic meniscus device 100 mimics the function of the natural meniscus and redistributes weight load transmitted across the knee joint.

As illustrated in FIG. 1, prosthetic meniscus device 100 has been inserted into the medial compartment of the native tibial plateau, according to an embodiment. Unlike conventional implants, prosthetic meniscus device 100 is not fixed to the bone or soft tissues of the knee joint. Instead, prosthetic meniscus device 100 floats inside the medial compartment between the femoral bearing surface and the native tibial plateau, and engages the femoral bearing surface and the native tibial plateau when the knee is in motion.

Figure 2:
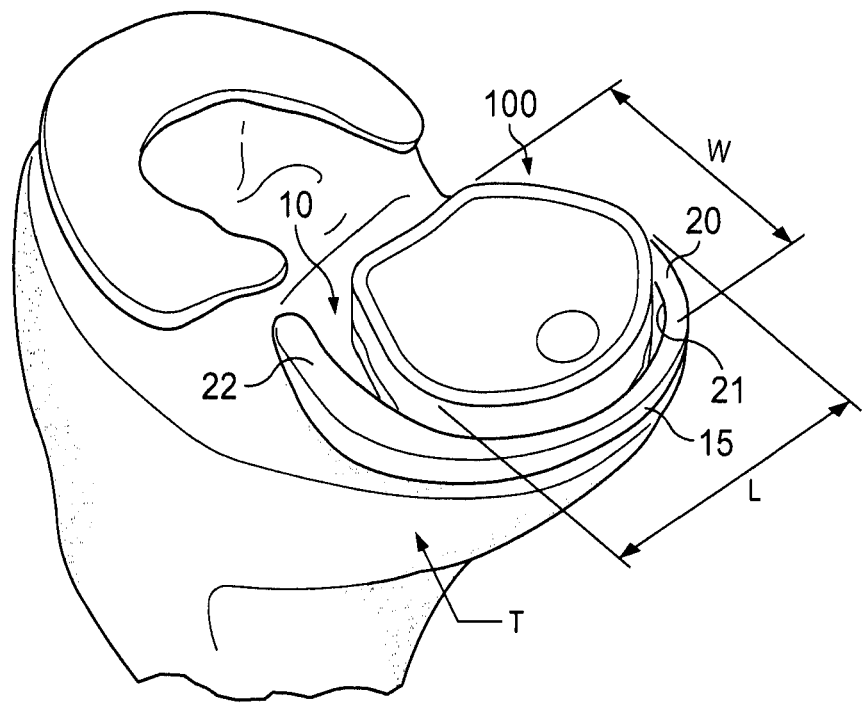
FIG. 2 is a perspective view of a prosthetic meniscus device disposed on a tibia according to an exemplary implementation.

FIG. 2 shows an example illustration of the prosthetic meniscus device 100 disposed upon the tibia T of a knee joint with an injured meniscus 10. The meniscus 10 includes an outer rim 15 that is anchored to the bone along the posterior rim 20 and the anterior rim 22. The meniscus may form a meniscus pocket defined by the outer rim of the meniscus, and in which the prosthetic meniscus device 100 may be disposed. The prosthetic meniscus 100 engages not only the tibia T, but also the femur (not shown in FIG. 2). The described positioning is true also when the natural remaining meniscus is not anchored or partially anchored. The last is sometimes the case after injury and/or in a degenerated joint.

In the illustrated embodiment, prosthetic meniscus device 100 is placed inside the native tibial plateau of the medial compartment. Importantly, the prosthetic meniscus device 100 is not fixed or attached to the native tibial plateau or to any other tissue and is free floating inside the medial compartment.

In other embodiments (not illustrated here), prosthetic meniscus device 100 may also be utilized in other joints about the body. In addition, it may be used in any of the other knee bearing surfaces and menisci, such as the right knee medial meniscus, left knee lateral meniscus, and/or right knee lateral meniscus. In that regard, the size, shape, thickness, material properties, and/or other properties of the prosthetic meniscus device 100 may be configured for each particular application, and also to the size and shape of the knee, knee joints, shoulder, hip, ankle, compromised and non-compromised meniscus, etc., of each patient.

Figure 3:
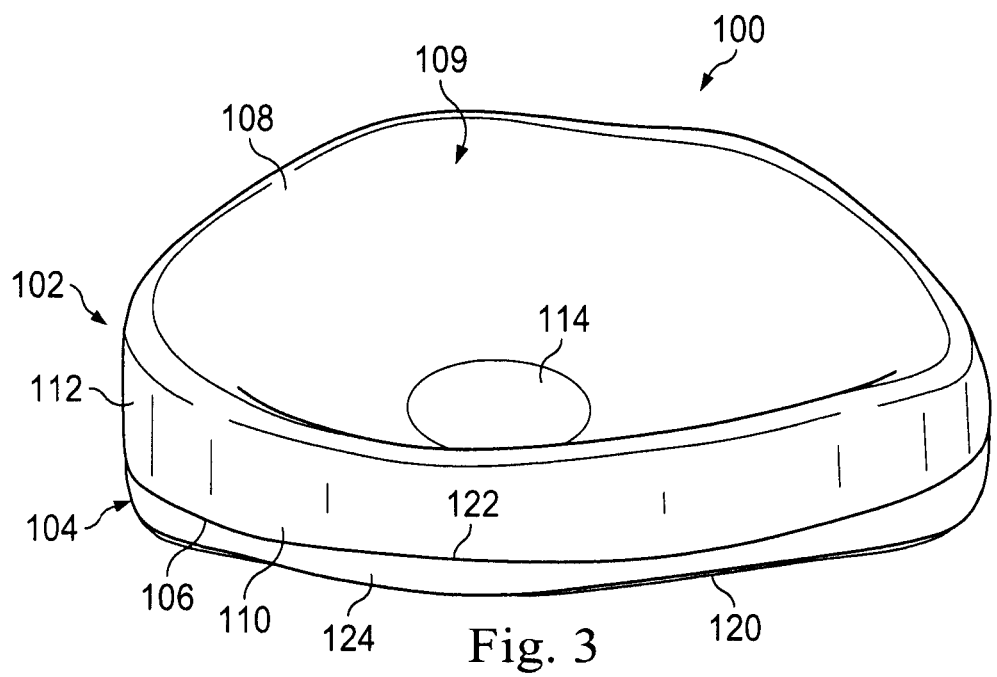
FIG. 3 is a perspective view of a prosthetic meniscus device according to an exemplary implementation.
Figure 4:
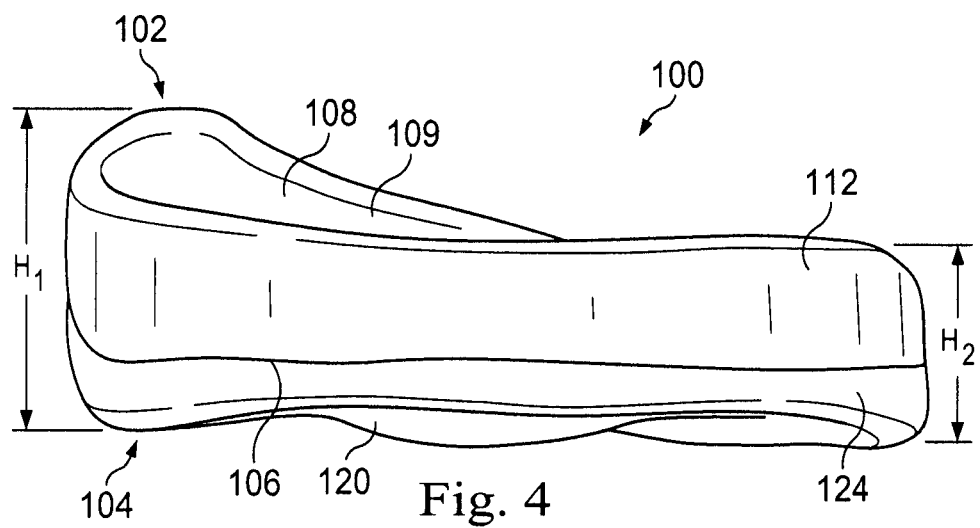
FIG. 4 is a side view of a prosthetic meniscus device according to an exemplary implementation.

FIGS. 3 and 4 are perspective and side views of the prosthetic meniscus device 100 according to an exemplary implementation. The prosthetic meniscus device 100 includes a meniscus component 102 and a base component 104. Here, the meniscus component 102 and the base component 104 are attached together into a single component along an interface line 106. The meniscus component 102 comprises a tissue-interfacing upper surface 108, interface surface 110, and a peripheral side surface 112.

The tissue interfacing upper surface 108 may be shaped with a concave receiving cavity or basin 109 that redistributes weight load transmitted across the knee joint while protecting the cartilage of the medial femoral condyle. The meniscus component 102 may conform to and fit the natural components of the knee joint, and also adapt to the changes of the natural components of the knee joint with time and use. In the illustrated embodiment, the tissue interfacing upper surface 108 is shaped and arranged to face the medial femoral condyle and may press or engage the cartilage of the medial femoral condyle or the femoral surface. In some embodiments, the tissue interfacing upper surface 108 may be custom molded to conform to or match the shape the cartilage of the medial femoral condyle of the host knee.

In some implementations, the tissue interfacing upper surface 108 may have one or more bone-relief recess areas, such as a bone-relief recess area 114 disposed in the receiving basin 109. Bone-relief recess area 114 is an indentation in the tissue interfacing upper surface 108 of the meniscus component 102. The bone relief recess area 114 may be manufactured by any method including molding, machining, etching, or other method. The bone-relief recess area 114 limits contact or engagement between the tissue interfacing upper surface 108 and the bone structure otherwise supported within the basin or concave shape of the tissue interfacing upper surface 108. For example, when the joint is a knee the bone-relief recess area 114 may limit contact or engagement between the tissue interfacing upper surface 108 and a portion of the medial femoral condyle that is opposite of the bone-relief recess area 114, while the tissue interfacing upper surface 108 still supports other portions of the medial femoral condyle. The bone-relief recess area 114 may be shaped as an additional divot, depression, or etch formed in the tissue interfacing upper surface 108.

Such limited contact between the tissue interfacing upper surface 108 and a portion of the adjacent bone may be provided for medical reasons, for general comfort, or for other reasons. For example, when certain areas of the cartilage and/or the bone at the treated joint have been damaged, further contact with prosthetic meniscus device 100 would exacerbate the damage or cause additional pain to the patient. In this case, when the meniscus component 102 with the bone-relief recess area 114 is inserted into the medial compartment such that the bone-relief recess area 114 faces the damaged portion of the femoral bearing surface, the bone-relief recess area 114 limits contact with the damaged surface and prevents further deterioration of the femoral bearing surface, while the remainder of tissue interfacing upper surface 108 still provides supportive contact with the non-damaged portions of the joint structure.

In another example, limited contact between the prosthetic meniscus device 100 and the femoral bearing surface may be necessitated after a patient underwent a minimally invasive surgery to replace or repair a portion of the cartilage of the medial femoral condyle. One way to replace or repair portions of the cartilage is to insert a biologic or stem cell paste into the damaged portions or the cartilage and allow the cartilage to regenerate and regrow. However, cartilage does not regenerate at a density required to bear weight in the knee joint unless pressure is applied to the cartilage. Hence, in order for the cartilage to regenerate at a necessary density, a patient should apply pressure on the knee and on the femoral bearing as the cartilage regenerates and regrows. In order for the patient to put pressure on the knee, yet for the biologic or the stem cell paste to have limited or no contact with the prosthetic meniscus device 100, the tissue interfacing upper surface 108 includes the bone-relief recess area 114 that faces the portion of the medial femoral condyle that has been injected with a biologic or stem cell paste. The bone-relief recess area 114 may prevent or may limit contact between the prosthetic meniscus device 100 and the portion of the medial femoral condyle that was injected with a biologic or the stem cell paste while the cartilage regenerates. Yet, at the same time, bone-relief recess area 114 also allows a patient to apply pressure to the knee that causes the cartilage to regenerate at a density that supports pressure on a knee joint.

In some implementations, the peripheral side surface 112 forms the outer peripheral surface of the meniscus component 102 that extends between and connects the tissue interfacing upper surface 108 and the interface surface 110. In some implementations, the peripheral side surface 112 is formed as a monolithic part of the meniscus component 102, and in some implementations, the peripheral side surface 112 is formed of a wall structure or peripheral bumper formed or molded about the main body portion of the meniscus component forming the tissue interfacing upper surface 108 and the interface surface 110. In some implementations, such as when the meniscus component 102 is formed of two elements joined together, the peripheral side surface 112 may have a circular or elliptical shape that surrounds and may be attached to the main body portion of the meniscus component 102. In such implementations, the peripheral side surface 112 may also comprise of a denser material than the rest of the meniscus component 102.

In some implementations, base component 104 comprises a tissue interfacing lower surface 120, an interface surface 122, and a peripheral side surface 124. Generally, the peripheral side surface 124 is a rigid support structure or wall that forms an outer periphery of the base component 104 and has a circular or an elliptical shape that imitates or substantially matches the shape of the peripheral side surface 112 of the meniscus component 102. In the example shown in FIG. 5, the peripheral side surface 124 is a substantially vertical wall surface. The tissue interfacing lower surface 120 is also of a circular or elliptical shape. The base component 104 is attached to the meniscus component 102 at the interface line 106, where the interface surface 110 of the meniscus component 102 is disposed in an abutting relationship with the interface surface 122 of the base component 104. Depending on the implementation, the interface line may be a location where the meniscus component 102 and the base component 104 are fused together, bonded together, or adhered together. In other implementations, the interface line is a contact region, where the meniscus component 102 and the base component 104 are in contact but not bonded together. In some implementations, this peripheral side surface 124 and the central region of the base component 104 together form a cup or basin in which the meniscus component 102 may be disposed.

As illustrated in FIGS. 3 and 4, in some implementations, the peripheral side surface 112 has a smooth interface with peripheral side surface 124, providing a smooth flush interface at the peripheral side surfaces and at the interface line 106.

In some implementations, the meniscus component 102 and the base component 104 may comprise the same or different materials. In some implementations, both of the meniscus component 102 and the base component 104 may comprise a polymeric material, with the meniscus component 102 having a less dense polymeric material than the base component 104. For example, the material of meniscus component 102 may be malleable and be designed to adjust and conform to changes in the medial femoral condyle of the femur and interact with the damaged cartilage in the medial femoral condyle. The base component 104, on the other hand, may comprise the same or different plastic material that is denser than the material of the meniscus component 102, a bio-compatible, non-reactive metal, or a ceramic material. The base component 104 functions to maintain the prosthetic meniscus device 100 in place in the natural tibial plateau in order to prevent unwanted expulsion of the prosthetic meniscus device 100 from the knee joint.

In some implementations, the base component 104 may be made of polycarbonate-urethane (PCU) or another similar medical grade plastic which may be of different density from the meniscus component 102. Typically, the base component 104 is more dense than that of the meniscus component 102. In another embodiment, base component 104 may be made of a bio-compatible, non-reactive metal, such stainless steel, cobalt chrome, or titanium, to name a few examples. In yet another embodiment, the base component 104 may be made of a bio-compatible ceramic material. In some implementations, the meniscus component is made of a polycarbonate-urethane and the base component is made of a bio-compatible metal.

Referring to FIGS. 3 and 4, the prosthetic meniscus device 100 is disc-shaped and may have a height H1 on a higher side that is different from the height H2 on a lower side. The heights H1 and H2 of the prosthetic meniscus device 100 may be selected to provide the most support and comfort to the bone and/or cartilage structure adjacent the joint. Because the prosthetic meniscus device 100 may be formed to match the adjacent bone and/or cartilage structures, the interface line 106 may follow the profile of the outer surfaces of the component 102 and the component 104.

The overall maximum height (in this example corresponding to height H1) may vary depending upon the measured location. For example, the nonplanar tissue interfacing upper surface 108 of the meniscus component 102 and the nonplanar tissue interfacing lower surface 120 of the base component 104 may impact the height at any particular location of the prosthetic meniscus device 100. Generally, in addition to the surface variations and shapes of the tissue interfacing upper surface 108, the height may be selected to fit within the available space between the femoral bearing surface and the natural tibial plateau of a host knee. In some implementations, the maximum height H may be between 0.5 mm and 15 mm. In some implementations, the maximum height (corresponding to H1) measured along the outer edges of the prosthetic meniscus device 100 may be about 10 mm and the minimum height, which may be measured in the central portion of the prosthetic meniscus device 100 may be about 2 mm. Other thicknesses or heights, both smaller and larger are contemplated. In one embodiment, both of height H1 and height H2 of the prosthetic meniscus device 100 may be between 5 mm and 30 mm.

The prosthetic meniscus device 100 also has a longitudinal length L and lateral width W, shown in FIG. 2. In some implementations, the longitudinal length L of prosthetic meniscus device 100 may be dictated by the distance between the anterior and posterior edges of the medial femoral bearing surface and the natural medial tibial plateau of a host knee. In some implementations, the longitudinal length L may be between 20 mm and 70 mm, although larger and smaller lengths are contemplated.

In some implementations, the lateral width W of the prosthetic meniscus device 100 may be the shortest measurable width of the prosthetic meniscus device 100 that is perpendicular to the longitudinal length L. Generally, the lateral width W may be dictated by the lateral width of the femoral condyle and the natural medial tibial plateau of a host knee. The lateral width W may be between 20 mm and 50 mm in some implementations, although larger and smaller lateral widths are contemplated.

An advantage of the prosthetic meniscus device 100 described herein is that the base component 104 also floats within the joint. Therefore, the natural meniscus and the supporting femur and tibia may remain intact. That is, since tissue penetrating anchors are not employed in some embodiments of the prosthetic meniscus device 100, additional trauma to the joint may be reduced or minimized when compared to conventional devices.

Figure 5:
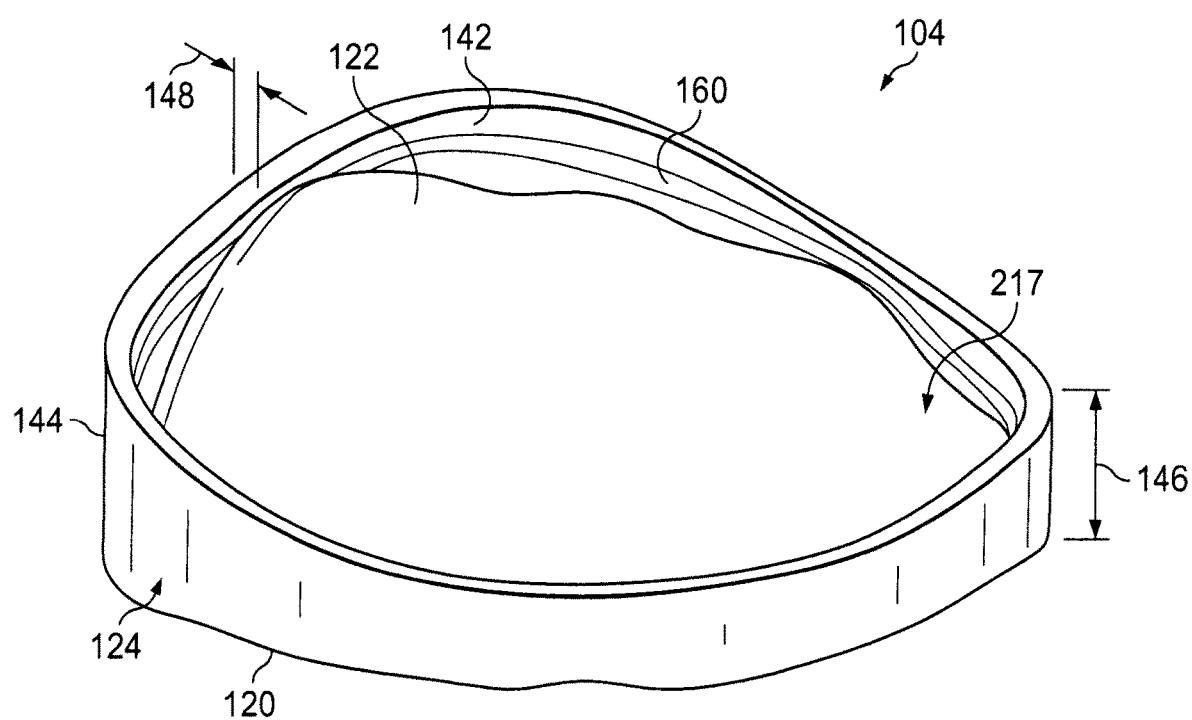
FIG. 5 is a perspective view of a meniscus component according to an exemplary implementation.

FIG. 5 is a perspective view of the base component 104 of the prosthetic meniscus device 100, according to an example implementation. The base component 104 may be formed of a rigid, supportive material such as a metal, a plastic, and/or a ceramic material. As illustrated in FIG. 3, the peripheral side surface 124 and the tissue interfacing lower surface 120 together form a basin-shape defining a containment cavity 140 that is shaped to receive and provide support to the meniscus component 102. The peripheral side surface 124 forms the peripheral wall of the base component 104 and comprises a radially-inwardly facing inner surface 142 and a radially-outwardly facing outer surface 144. In some implementations, these surfaces 142, 144 have portions that are substantially parallel. The inner surface 142 of the base component 104 faces an outwardly facing surface of the meniscus component 102 when the meniscus component 102 is disposed therein. In some embodiments, inner surface 142 may be a smooth surface and may be arranged to prevent the meniscus component 102 from translating in the containment cavity 140. In other implementations, the inner surface of the base component 104 may be shaped and sized to accommodate translation or displacement, such as by sliding for example of the meniscus component 102.

In some implementations, the outer surface 144 of base component 104 may be shaped to be positioned inside the boundaries of the host joint, such as, for example, within a medial compartment of the knee. This may permit the outer surface 144 to be surrounded by the meniscus in the native tibial plateau. In some implementations, the base component 104 may be positioned within boundaries of the joint, such as the native tibial plateau such that the tissue interfacing lower surface 120 is adjacent and conforms to the shape of the meniscus inside the native tibial plateau. The base component 104 can be positioned also in instances where there is a limited/partial or even no remaining meniscus at all.

As shown in FIG. 5, the interface surface 122 of the base component 104 may be molded to have a non-planar, uneven surface that may be arranged to match the interface surface 110 of the meniscus component 102. In some implementations, the tissue interfacing lower surface 120 may be molded to fit the underlying bone structure against which it abuts. For example, when the base component 104 is a knee implant, the tissue interfacing lower surface 120 may be shaped to fit a native tibial plateau and/or the meniscus surrounding the native tibial plateau, such that the native tibial plateau and the meniscus provide support for keeping the base component 104 in place. Since the tissue interfacing lower surface 120 abuts directly against and interfaces with the bone structure, such a form-fit surface may help maintain the base component 104 in place. That is, variations in the height of the surfaces may be selected to match the anatomical features of the patient in some embodiments in the manner of a natural meniscus. The base component 104 can be positioned and stay stable also in instances where there is only a limited/partial or even no meniscus at all.

In some implementations, the height 146 of the peripheral side surface 124 or wall may vary between a maximum height in the range of 10 mm to 20 mm and may vary between a minimum height of 2 mm to 10 mm depending upon the location and/or the size of the patient. Height variations may be due to the preformed shape of the tissue interfacing lower surface 120 to coincide with the interface surface 110 of the meniscus component 102 and/or with the shaped of the adjacent bone and/or cartilage structures, such as the native tibial plateau. In some implementations, the height 146 of peripheral side surface 124 varies from a maximum height of 20 mm to a minimum height of 10 mm. In other implementations, the height 146 varies from a height of 15 mm to a height of 5 mm. Other amounts are also contemplated. In some implementations, the wall thickness 148 of the peripheral side surface 124 measured between inner surface 142 and the outer surface 304 may be between 0.1 mm and 3 mm. In one particular embodiment, the wall thickness 148 may be about 1 mm.

In this implementation, the inner surface 142 of the peripheral side surface 124 includes a locking structure 160. In this implementation, the locking structure 160 is a groove or recess that extends along the inner surface 142 of the peripheral side surface 124 and circumscribes the containment cavity 140. The locking structure 160 is shaped and formed to receive a corresponding projecting nub on the meniscus component 102 to secure the meniscus component 102 in the containment cavity 140, thereby mechanically securing the meniscus component 102 to the base component 104. As indicated above, the base component 104 may be formed of a rigid material that may provide support to the softer meniscus component 102. In some implementations, a depth of the containment cavity is less than half a width of the base component 104. This may contribute to the disc-shaped nature of some implementations of the prosthetic meniscus device 100.

Figure 6:
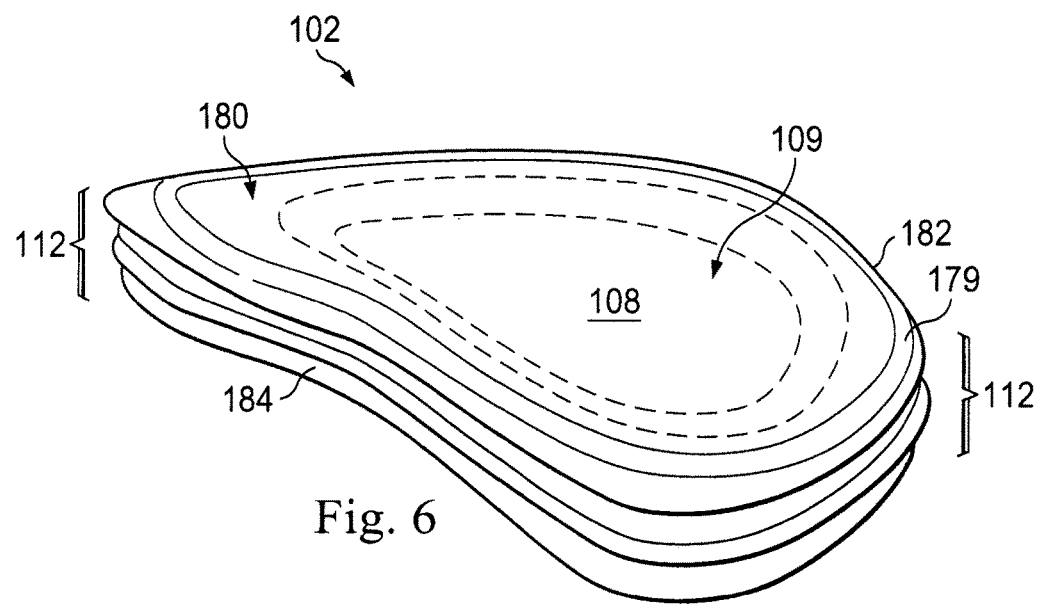
FIG. 6 is a perspective view of a meniscus component meniscus device according to an exemplary implementation.
Figure 7:
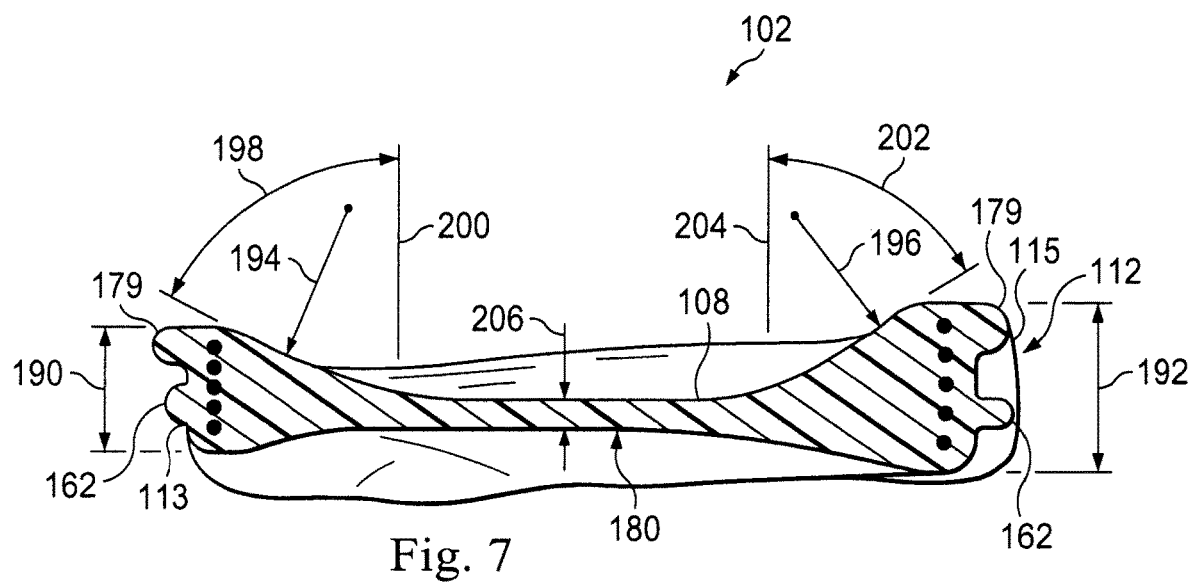
FIG. 7 is a cross-sectional view of a meniscus component according to an exemplary implementation.

FIGS. 6 and 7 show the meniscus component 102 of the prosthetic meniscus device 100. Some features may be similar to a prior design set forth in U.S. Pat. No. 8,361,147, which is hereby incorporated by reference in its entirety. The meniscus component 102 comprises the peripheral side surface 112 and a central body portion 180. Generally, the peripheral side surface 112 has an increased thickness and height relative to the central body portion 180. In some instances the peripheral side surface 112 has a thickness between 5 mm and 15 mm. In some instances, the central body portion 180 has a thickness between 0.5 mm and 5 mm. In some particular implementations, the peripheral side surface 112 has a maximum thickness of approximately 10 mm and the central body portion 180 has a maximum thickness of approximately 2 mm. The height or thickness of the peripheral side surface 112 varies around the perimeter of the prosthetic device in some instances. In that regard, the variations in the height or thickness of the peripheral side surface 112 are selected to match the anatomical features of the patient in some embodiments. Similarly, the height or thickness of the central body portion 180 varies across the prosthetic device in some embodiments. Again, the variations in the height or thickness of the central body portion 180 are selected to match the anatomical features of the patient in some embodiments.

In some implementations, and with reference to FIG. 6, the peripheral side surface 112 extending about the periphery of the meniscus component 102 may be divided into two or more segments, each having different heights or properties. For example, in some implementations, the peripheral side surface 112 includes a first portion 182 and a second portion or bridge 184. In some embodiments, the first portion 182 substantially matches the shape of a natural meniscus. In some embodiments, the peripheral side surface 112 has a circular or semi-ellipsoidal shape. Accordingly, the first portion 182 extends around a majority of the peripheral side surface 112. In some implementations, this may form a convex portion of the outer surface. The bridge 184 may connect the two ends of the first portion 182. Thus, where the prosthetic device 100 is configured for use as a medial meniscus device, the bridge 184 may extend along the lateral side of the prosthetic meniscus device 100. Where the prosthetic meniscus device 100 is configured for use as a lateral meniscus device, the bridge 184 may extend along the medial side of the device. Accordingly, the peripheral side surface 112—comprised of the first portion 182 and the bridge 184 and having an increased thickness relative to the central body portion 180—completely surrounds the central body portion 180 and serves to limit movement of the prosthetic device after implantation.

The height or thickness of the bridge 184 is based on the size of the femur notch and the distance to the cruciate ligaments in some embodiments. In some embodiments, the bridge 184 has a maximum height or thickness that is between ¼ and ¾ the maximum height or thickness of the first portion 182 of the peripheral side surface 112. In some embodiments, the size and shape of the bridge 184 is selected to achieve an optimal pressure distribution on the native tibial plateau in order to mimic the pressure distribution of a healthy natural meniscus. The bridge 184 and, more generally, the peripheral side surface 112 are geometrically characterized by anterior, posterior, lateral-anterior, mid-lateral and lateral-posterior angles and heights as well as sagittal and coronal radii of curvature.

The central body portion 180 defines tissue interfacing upper surface 108 and the interface surface 110. The tissue interfacing upper surface 108 may interface with the bone and/or cartilage structures of the host joint and may form a part of a bearing surface. In particular, the tissue interfacing upper surface 108 is configured to engage with a medial femoral condyle of the femur. In some embodiments, the tissue interfacing upper surface 108 includes both a vertical and horizontal surface. To that end, in some embodiments the tissue interfacing upper surface 108 comprises a concave surface forming the basin 109 that defines the vertical and horizontal surfaces. The thickness of the central body portion 180 between the tissue interfacing upper surface 108 and the interface surface 110 supports stress distribution capability of the component, while the increased height of the tissue interfacing upper surface 108 as it extends outwardly towards the peripheral side surface 112 defines the horizontal surface of the component. Similarly, in some embodiments the interface surface 110 includes both vertical and horizontal components. In particular, in some embodiments the interface surface 110 comprises a convex surface or a concave surface that is molded to the shape of the inside portion of base component 104.

The thickness of the central body portion 180 between the tissue interfacing upper surface 108 and the interface surface 110 determines the load distribution capacity of the component, while the tapered height of the tissue interfacing upper surface 108 as it extends outwardly towards the peripheral side surface 112 defines the horizontal component. In some embodiments, the tissue interfacing upper surface 108 and/or the interface surface 110 are shaped such that the component is biased towards a neutral position in the knee. For example, the arcuate profiles of the tissue interfacing upper surface 108 and/or the interface surface 110 are shaped such that the interaction between the surfaces and the femoral surface encourages the implant to a particular orientation relative to the surfaces.

Referring to FIG. 7, shown therein is a diagrammatic cross-sectional view of the meniscus component 102 taken along an anterior to posterior section line between an anterior end 113 and posterior end 115. As shown, the anterior end 113 of the meniscus component 102 has an anterior height or thickness 190. In that regard, the anterior height or thickness 190 of the anterior end 113 is between about 4 mm and immediately adjacent bridge 184 could be as great as about 15 mm and, in some instances, is between about 5.7 mm and about 9.3 mm. In the illustrated embodiment, the anterior height or thickness 190 of the anterior end 113 is approximately 7.8 mm. In a smaller embodiment, the anterior height or thickness 190 is approximately 5.7 mm. In a larger embodiment, the anterior height or thickness 190 is approximately 9.3 mm. The posterior height or thickness 192 of the posterior end is between about 4 mm and immediately adjacent the bridge 184 could be as great as about 20 mm and, in some instances, is between about 7.7 mm and about 12.7 mm. In the embodiment, the posterior height or thickness 192 of the posterior end 115 is approximately 9.0 mm. In a smaller embodiment, the posterior height or thickness 192 is approximately 7.7 mm. In a larger embodiment, the posterior height or thickness 192 is approximately 12.7 mm.

The anterior portion of the upper surface of the anterior end 113 has an anterior radius of curvature 194. In that regard, the anterior radius of curvature 194 is between about 10 mm and about 100 mm and, in some instances, is between about 23.0 mm and about 33.1 mm. In the embodiment, the radius of curvature 194 is approximately 72 mm. In another embodiment, the radius of curvature 194 is approximately 28 mm. In a smaller embodiment, the radius of curvature 194 is approximately 23 mm. In a larger embodiment, the radius of curvature 194 is approximately 33.1 mm. The posterior portion of the upper surface of the posterior end 115 has a posterior radius of curvature 196. In that regard, the posterior radius of curvature 196 is between about 5 mm and about 70 mm and, in some instances, is between about 15.2 mm and about 24.2 mm. In the illustrated embodiment, the radius of curvature 196 is approximately 30 mm. In a smaller embodiment, the radius of curvature 196 is approximately 15.2 mm. In a larger embodiment, the radius of curvature 196 is approximately 24.2 mm.

Further, the anterior end 113 of the upper surface generally extends at an anterior angle 198 with respect to an axis 200 extending substantially perpendicular to a plane generally defined by the free floating meniscus component 102, as shown. The anterior angle 198 is between about 45 degrees and about 75 degrees and, in some instances, is between about 62 degrees and about 68 degrees. In the illustrated embodiment, the angle 198 is approximately 65 degrees. In a smaller embodiment, the angle 198 is approximately 62 degrees. In a larger embodiment, the angle is approximately 68 degrees. The posterior end 115 of the upper surface generally extends at an posterior angle 202 with respect to an axis 204 extending substantially perpendicular to a plane generally defined by the prosthetic meniscus device 100, as shown. The posterior angle 202 is between about 35 degrees and about 70 degrees and, in some instances, is between about 55 degrees and about 61 degrees. In the embodiment, the angle 202 is approximately 58 degrees. In a smaller embodiment, the angle 202 is approximately 50 degrees. In a larger embodiment, the angle 202 is approximately 65 degrees.

The central body portion 180 has a height or thickness 206 between the articulating tissue interfacing upper surface 108 and the interface surface 110. In some embodiments, the height or thickness 206 is the minimal thickness of the central body portion 180 and, in more specific embodiments, the minimal thickness of the entire free floating meniscus component 102. To that end, the height or thickness 206 is between about 1 mm and about 3 mm and, in some instances, is between about 1.2 mm and about 2.1 mm. In the embodiment, the height or thickness 206 is approximately 1.5 mm. In a smaller embodiment, the height or thickness 206 is approximately 1.2 mm. In a larger embodiment, the height or thickness 206 is approximately 2.1 mm.

In the implementation shown, the peripheral side surface 112 of the meniscus component 102 comprises a locking structure 162 and a shoulder 179. The locking structure 162 extends along the peripheral side surface 112 and arranged to secure the meniscus component 102 in the base component 104. In the implementation shown, the locking structure 162 is a protruding nub that extends radially outwardly from the peripheral side surface 112. In the embodiment shown, the protruding nub extends completely around the peripheral surface of the meniscus component 102. In other implementations, the protruding nub may extend only partially around the peripheral surface of the meniscus component 102. The protruding locking structure 162 is shaped and sized to fit into the locking structure 160 and the base component 104. Accordingly, some implementations of the meniscus component may be snapped fitted into the base component 104. The cooperating locking structures 160, 162 may secure the component 102 to the base component 104 in a manner that safely prevents relative motion of one meniscus device component to the other.

The shoulder 179 of the peripheral side surface 112 may be a radially extending projection that may be disposed to overlie the upper edge of the peripheral side surface 124 of the base component 102. This arrangement is best seen in FIG. 8.

Figure 8:
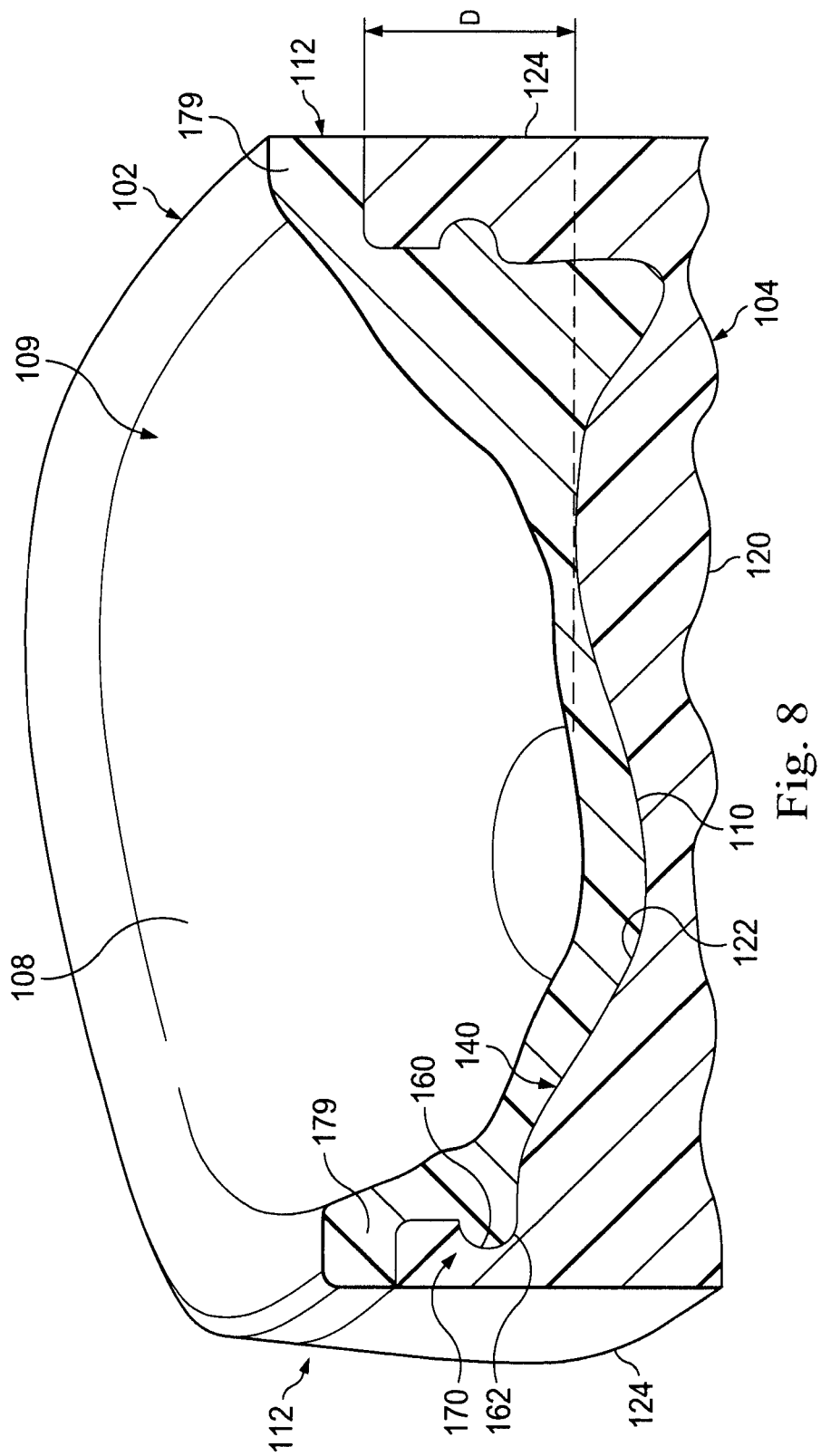
FIG. 8 is a perspective view of a cross-section of a prosthetic meniscus device according to an exemplary implementation.

FIG. 8 is a cross-sectional view of the prosthetic meniscus device 100 with the meniscus component 102 disposed inside the containment cavity 140 of the base component 104. As illustrated in FIG. 8, the interface surface 110 of the meniscus component 102 is disposed adjacent to the interface surface 122 of the base component 104. As also illustrated in FIG. 8, the tissue interfacing upper surface 108 is formed to have a concave surface, and is also formed to fit and conform to the nonplanar interface surface 122 of the base component 104. In some implementations, the tissue interfacing lower surface 120 of the base component 104 is also formed with a concave surface forming a basin shaped to receive and interface with bone structure at the joint. In the example shown, the tissue interfacing lower surface 120 is shown as relatively flat or planar, however, other implementations have a shape to match the interfacing tissue of the host joint.

The cross-sectional view also shows the locking structure 160 of the base component 104 and the locking structure 162 of the meniscus component 102. As indicated previously, this implementation includes a protruding nub and a receiving groove that mechanically prevents removal of the meniscus component 102 from the base component 104. In some implementations, the meniscus component contains the groove and the base component contains the protruding nub.

The meniscus component 102 may be formed of a material selected to provide some flexion and deflection under normal load. This may permit the meniscus component 102 to conform to tissue being supported thereby distributing weight across the bearing surface of the tissue. This may provide more comfort to the host joint while still providing suitable rigid support. The bottom of the receiving basin 109 of the meniscus component 102 is disposed below the upper edge of the peripheral side surface 124 of the base component 104. As such, patient tissue supported by the meniscus component 102 will be received into the containment cavity 140 of the base component. In FIG. 8, the depth of the basin 109 below the top edge of the peripheral side surface 124 is indicated by depth D. This arrangement may permit the peripheral side surface 124 of the base component 104 to provide radial support and reinforcement to the meniscus component 102. Accordingly, in implementations where the meniscus component 102 is selected of a material deformable over time under typical loading at the joint, the deformation may occur with the meniscus component 102, but the base component 104 may remain rigid to provide additional support and backing to the meniscus component 102. This may limit radial expansion of the meniscus component 102. In some examples, the depth D is selected to be between 0.5 mm and 20 mm. In some examples, the depth D is selected to be between about 3 mm and 30 mm, although larger and smaller depths are contemplated!

In some implementations, the peripheral side surface 124 may be formed of a more rigid material than the meniscus component 102, and may provide back-up, supporting rigidity and strength to the meniscus component 102. However, other arrangements may be used to securely maintain the meniscus component 102 in place within the base component 104. In some implementations, the meniscus component 102 and the base component 104 are formed of the same material. Although shown with a groove and a nub, other implementations may include one or more extending ridges, hooks, or notches that may extend into one or more of the tension apertures to fixedly attach the meniscus and base components 102, 104. In some implementations, the ridges, hooks, or notches may extend into other grooves or reception cavities formed in the outer edge of the meniscus component. These types of arrangements may provide mechanical interference that prevents the meniscus component 102 from displacing vertically relative to the base component 104.

In use, under a bearing load, the interface surface 110 of the meniscus component 102 may be formed to match the profile of the more rigid interface surface 122 of the base component 104. Under load, the concave cavity of the meniscus component 102 may change shape slightly, such as the radius of curvature may be increased as a result of the applied loading. Additionally, in some implementations, the outer radial portions of the meniscus component 102 may deform or expand under load. As described herein, the base component 102 may prevent over expansion and may provide stabilizing support to the meniscus component 102. However, in other implementations, fibers or other materials may be used to limit, restrain, or control, the amount of deformation permitted under a load.

As discussed above, the prosthetic meniscus device 100 is a minimally invasive implant that floats inside the medial compartment of the knee joint and may reduce or prevent further damage to the meniscus. The prosthetic meniscus device 100 also may protect a biologic in the medial femoral condyle while the biologic regenerates and regrows the damaged cartilage. In some implementations, the prosthetic meniscus device 100 may be implanted into the native tibial plateau of the host knee such that the meniscus component 102 engages the femoral surface and redistributes weight load transmitted across the knee joint, while the base component 104 engages the natural tibial plateau. As discussed above, the meniscus component 102 may be modified to have limited contact with one or more portions of the femoral surface as dictated by the treatment. For example, when the damaged area of the medial femoral condyle has been treated with a biologic or stem cell paste to allow cartilage to regenerate and regrow, the meniscus component 102 may include one or more bone-relief recess areas, such as bone-relief recess area 114 that limits contact between the prosthetic meniscus device 100 and the treated areas of the medial femoral condyle. Depending upon the implementation, the bone relief recess areas may be custom formed to match individual patients or conditions.

In some implementations, the meniscus component 102 with the bone-relief recess area 114 may be removed from the base component 104 and may be exchanged for another meniscus component 102 with a different bone-relief recess area 114 or for the meniscus component 102 with a smooth tissue interfacing upper surface 108. In some implementations, this may happen during presurgery planning or in the operating room as the need arises. Accordingly, the surgeon may have a plurality of meniscus component's 102, each of varying in areas of support or in location of a bone relief recess area 114. In other implementations, the meniscus component 102 may be exchanged for another after the medial femoral condyle has healed and the cartilage had regrown. In this implementation, the meniscus component 102 with the bone-relief recess area 114 may be exchanged in a revision surgery for the meniscus component 102 with the smooth tissue interfacing upper surface 108.

In some implementations, the prosthetic meniscus device 100 may be implanted in a two-step process. In the first step, only a temporary meniscus component 102 may be implanted into the knee joint. The implanted meniscus component 102 may comprise a smooth tissue interfacing upper surface 108 or have one or more bone-relief recess areas, such as bone-relief recess area 114 formed, such as by etching or machining, on the tissue interfacing upper surface 108, depending on the treatment. For example, a patient may be required to gradually apply pressure on the cartilage in the knee following a minimally invasive surgery in order for the cartilage to regrow and have necessary density, as described above. The meniscus component 102 having a smooth tissue interfacing upper surface 108 with the bone-relief recess area 114 opposite the areas in the medial femoral condyle where the cartilage is being regrown, allows the patient to apply pressure across the entire knee joint, including the areas where the cartilage is being regrown, yet limits the physical contact with these areas and the meniscus component 102.

In some implementations, the second step of the two-step surgical process may be performed days, weeks, months or even years after the first step of the surgical process. This may allow some healing to occur prior to the second step. For example, the second step of the two-step surgical process may be performed after cartilage has begun growing on the medial femoral condyle or other bone structure. In the second step, the meniscus component 102 may be replaced with a full prosthetic meniscus device 100, including the meniscus component 102 and the base component 104. The meniscus component 102 can be the same or different meniscus component 102 as in the first step. In some implementations, the meniscus component 102 may have a smooth tissue interfacing upper surface 108. As indicated herein, the second step generally occurs after the cartilage has healed or has been regrown and the prosthetic meniscus device 100 is implanted into the knee joint for the long term use by the patient.

Figure 9:
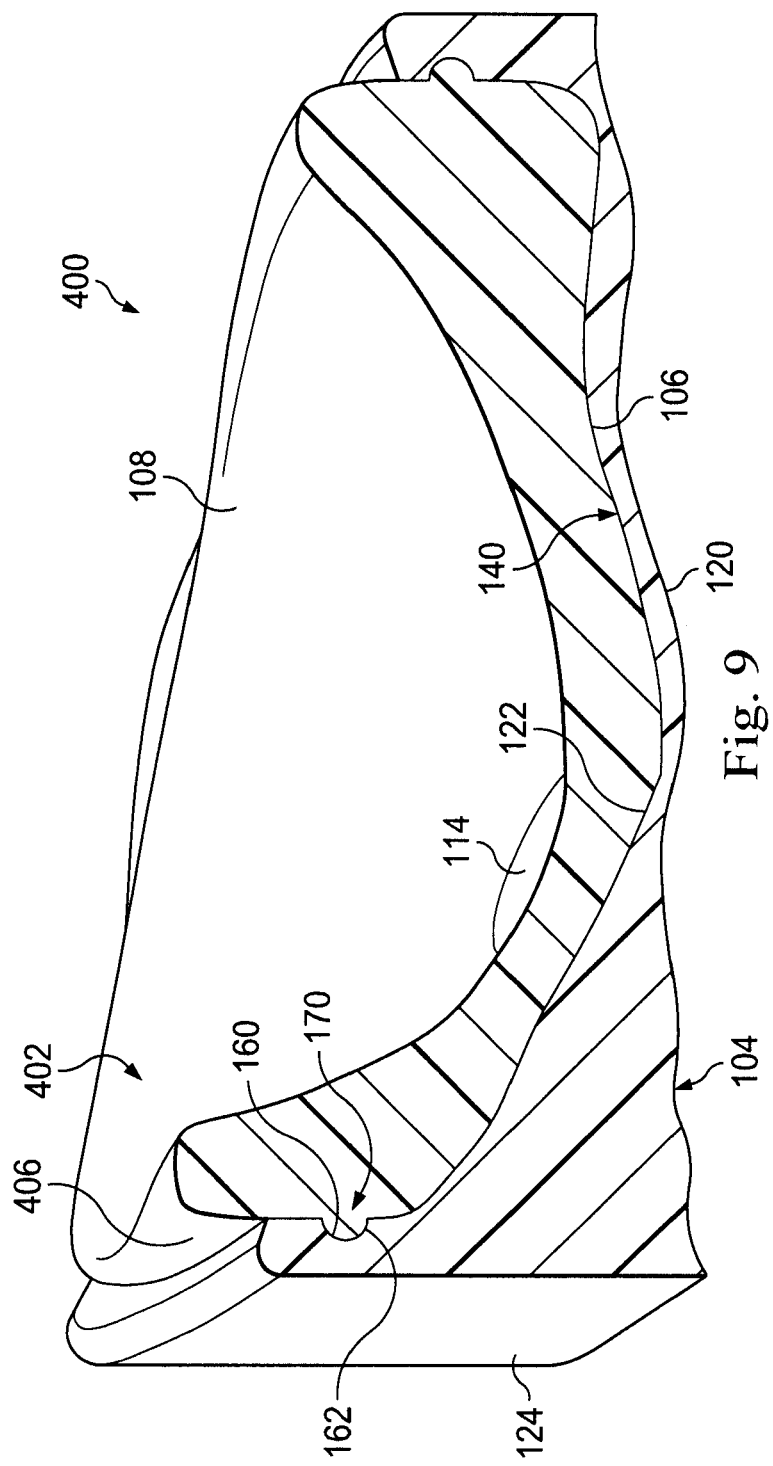
FIG. 9 is a perspective view of a cross-section of another prosthetic meniscus device according to an exemplary implementation.
Figure 10:
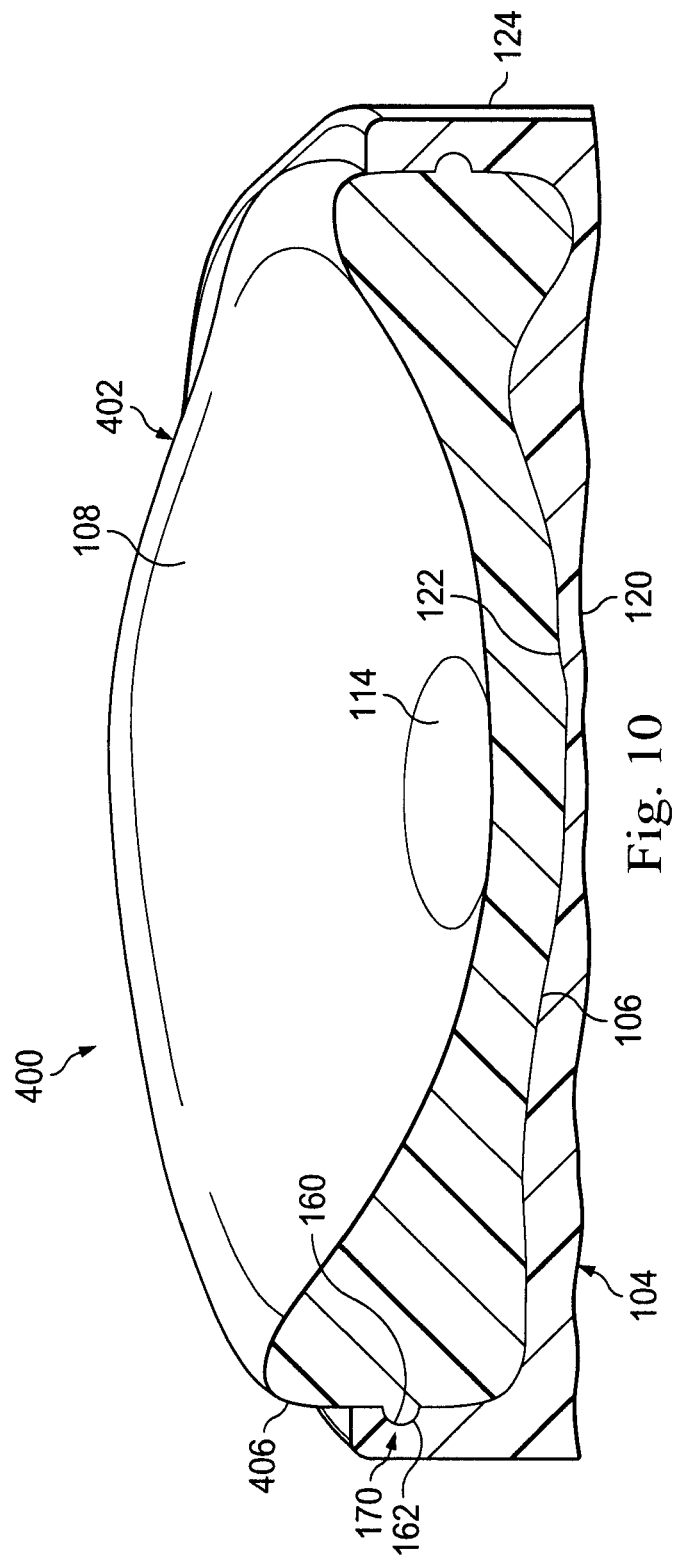
FIG. 10 is a perspective view of a cross-section of another prosthetic meniscus device according to an exemplary implementation.

FIGS. 9 and 10 show an additional embodiment of a prosthetic meniscus device 400 including a meniscus component 402 and the base component 104. FIG. 9 shows a cross-section taken and a posterior-anterior direction. FIG. 10 shows a cross-section taken transverse to the posterior-anterior direction. This embodiment differs from the prosthetic meniscus device 100 in that the outer walls of the meniscus component 402 do not extend over the outer wall of the base component 104. Other features will not be re-described. Accordingly, the meniscus component 402 may include an outer peripheral surface 406 that forms a substantially vertical wall. As can be seen, the meniscus component 402 still protrudes above the upper edge of the base component 104. In some implementations, this may permit the interface of the bone structure supported by the meniscus component 402 to reduce or eliminate a chance of contact with the base component 104. In this implementation, the locking mechanism 170 is still shown.

Figure 11:
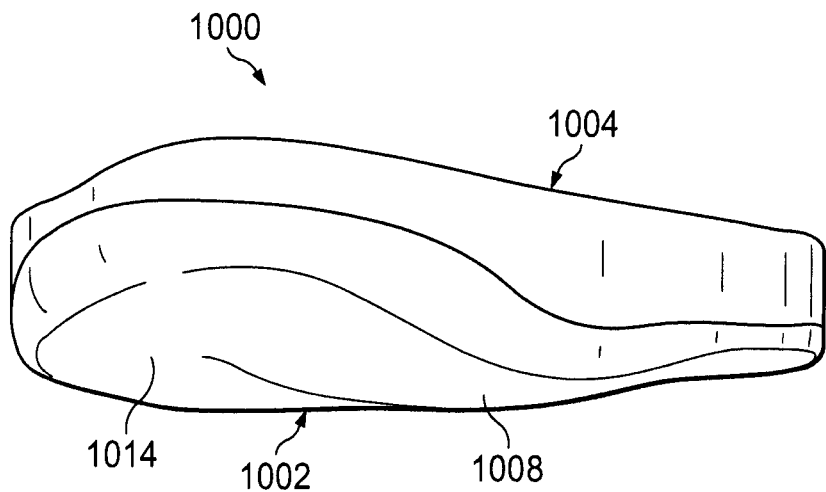
FIG. 11 is a perspective view of a prosthetic meniscus device according to an exemplary implementation.
Figure 12:
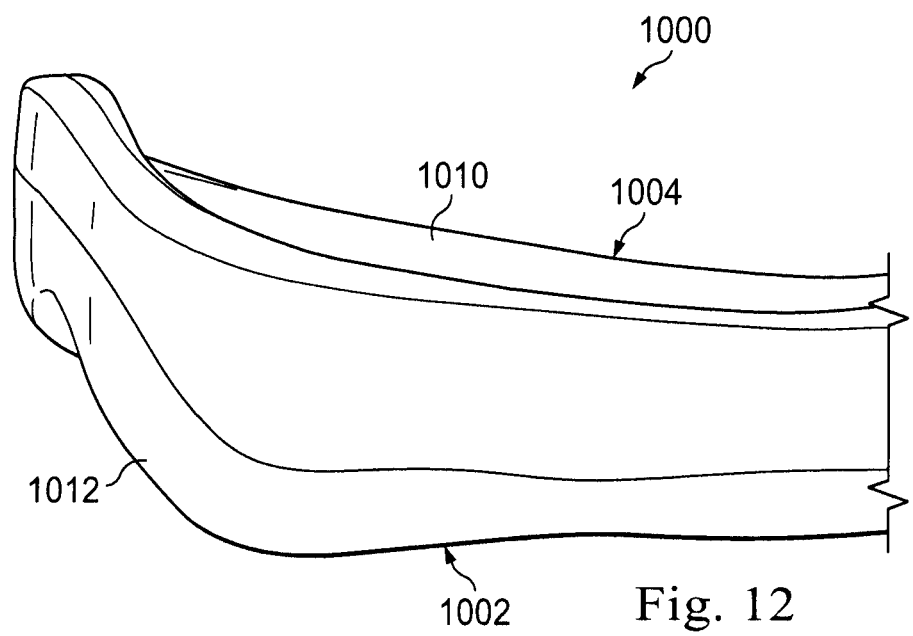
FIG. 12 is a perspective view of a prosthetic meniscus device according to an exemplary implementation.
Figure 13:
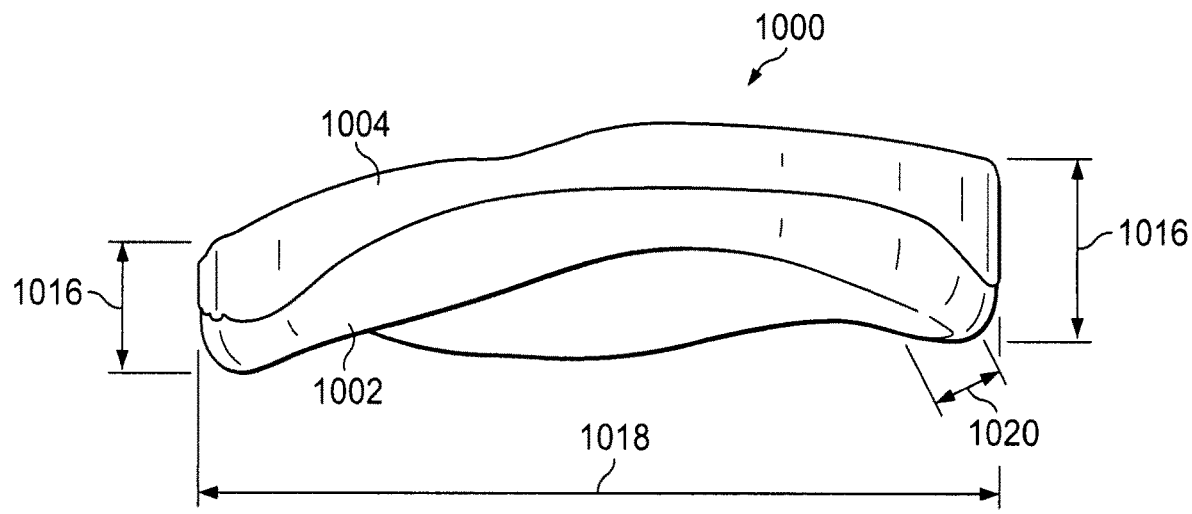
FIG. 13 is a perspective view of a prosthetic meniscus device according to an exemplary implementation.

FIGS. 11, 12, and 13 illustrate additional alternative embodiments of the prosthetic meniscus device 900, referred to as prosthetic meniscus device 1000. Referring to FIGS. 11-13, the prosthetic meniscus device 1000 is an inverted version of the prosthetic meniscus device 900 that is inserted into the knee joint upside down. As illustrated in FIG. 11, the prosthetic meniscus device 1000 comprises components 1002 and 1004. In an embodiment, component 1002 is analogous to the free floating meniscus component 102 and component 902, and component 1004 is analogous to the base component 104 and component 904. However, unlike component 902 that engages a femoral surface, component 1002 engages the natural tibial plateau in the knee joint. And, unlike component 904 that engages the natural tibial plateau, component 1004 engages the femoral surface. As such, component 1004 functions to maintain prosthetic meniscus device 1000 in place inside the medial compartment and prevents unwanted expulsion of the prosthetic meniscus device 1000 from the knee joint.

In the illustrated embodiment in FIG. 11, the bottom surface 1008 of component 1002 may be molded to shape the native tibial plateau and may generally be of a convex shape. As illustrated in FIG. 12, an upper surface 1010 of component 1004 may be molded to shape the medial femoral condyle of the femur surface and may be of a concave shape. In some implementations, component 1002 and component 1004 may be comprised of the same or different plastic materials, as materials described for components 902 and 904.

In some implementations, the prosthetic meniscus device 1000 may comprise an outer portion 1012 forming a peripheral sidewall. As illustrated in FIG. 12, the outer portion 1012 may form a smooth outer surface that seamlessly fuses components 1002 and 1004. As such, the outer portion 1012 may be comprised of the material of component 1002 and of component 1004 that are fused along the fused line 1006.

In an embodiment, just like the free floating meniscus component 102, component 1002 may have a bone-relief recess area 1014 (FIG. 11). The bone-relief recess area 1014 may limit or minimize contact between the portion of the native tibial plateau and the prosthetic meniscus device 1000.

Referring to FIG. 13, the prosthetic meniscus device 1000 has a thickness or height 1016, longitudinal width 1018, and lateral width 1020. The lateral width 1020 may be perpendicular to the longitudinal width. In an embodiment, thickness or height 1016 may vary according to the molded lower and upper surfaces of components 1002 and 1004. Also thickness or height 1016 may be dictated by the size of the medial compartment of the knee joint and the positioning of the prosthetic meniscus device 1000 inside the medial compartment. In an embodiment, the thickness or height 1016 of the prosthetic meniscus device 1000 may be between 0.5 mm and 15 mm. In some implementations, longitudinal width 1018 may be between 25 mm and 70 mm, and the lateral width 1020 may be between 20 mm and 50 mm. In a further embodiment, the longitudinal width 1018 and lateral width 1020 may be dictated by the size of the medial compartment of the knee joint.

Figure 14:
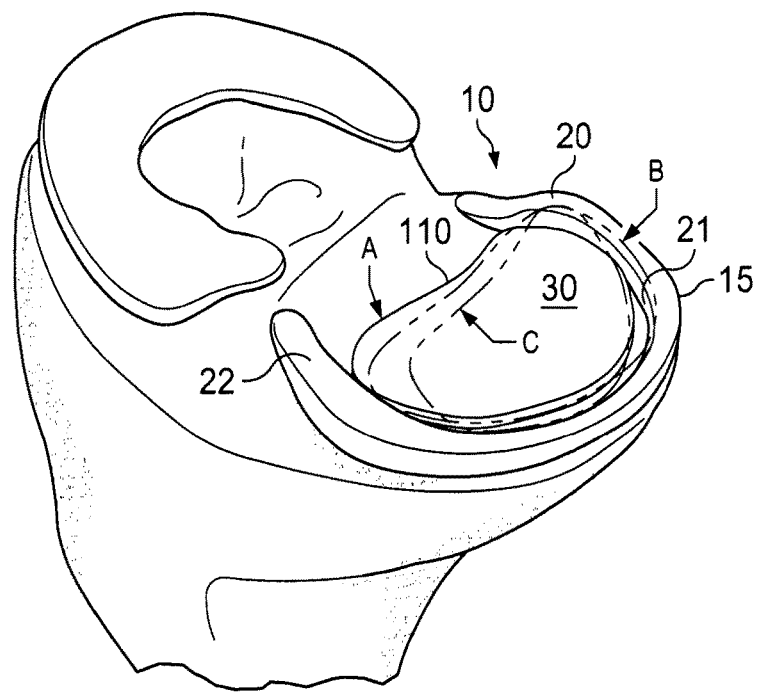
FIG. 14 is a perspective view of a prosthetic meniscus device disposed on a tibia according to an exemplary implementation.

Referring now to FIG. 14, there is shown a top view of a knee joint with an injured meniscus 10. The meniscus includes the outer rim 15 that is anchored to the bone along the posterior rim 20 and the anterior rim 22. In FIG. 14, the torn segments along with the undamaged central meniscus have been removed to expose the underlying tibia and define the implantation area as a meniscus pocket 30. The meniscus pocket 30 is bounded by sidewall 21. A prosthetic meniscus device 100 (not shown in FIG. 14) according to one aspect of the current disclosure is positionable in the meniscus pocket 30 defined by the sidewall 21, consistent with FIG. 2. As will be explained in greater detail below, the prosthetic meniscus free-floats within the meniscus pocket 30 to move into positions A, B and C. In that regard, the positions A, B, and C can be longitudinally, rotationally, and/or laterally offset from one another.

Figure 15A:
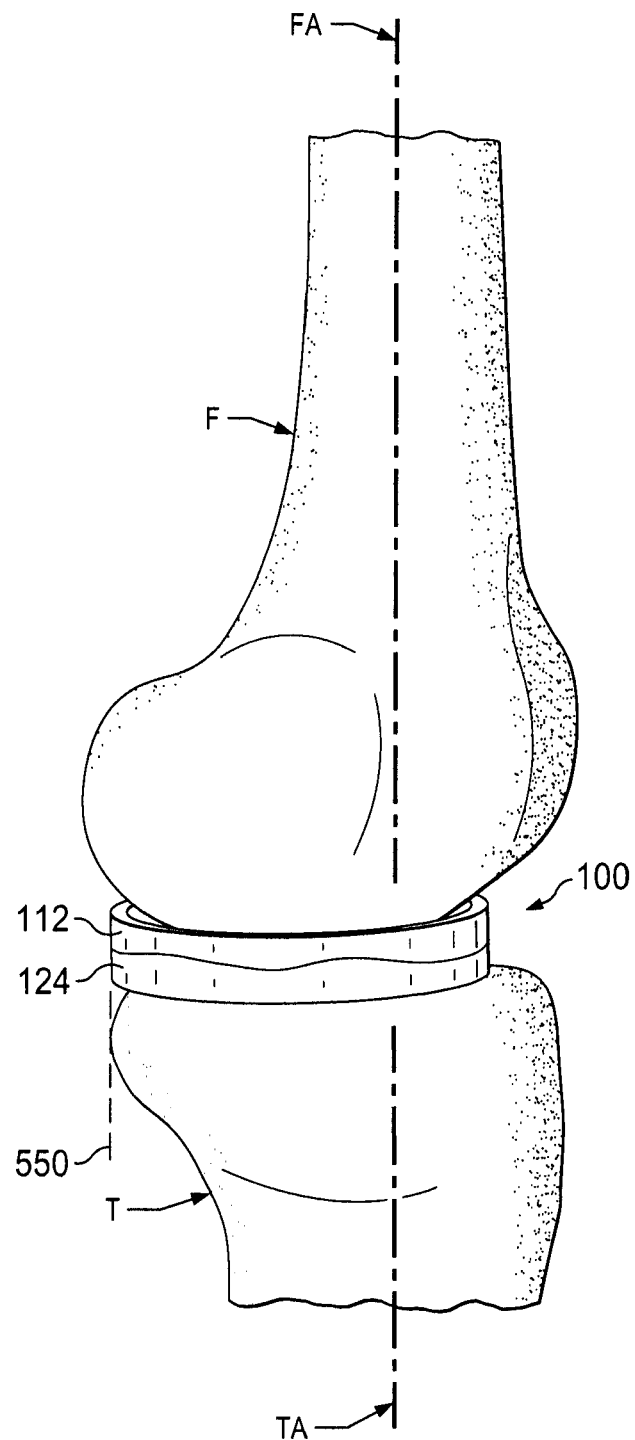
FIGS. 15A, 15B, and 15C illustrate an implanted prosthetic meniscus device with the knee articulated through a series of angles.
Figure 15B:
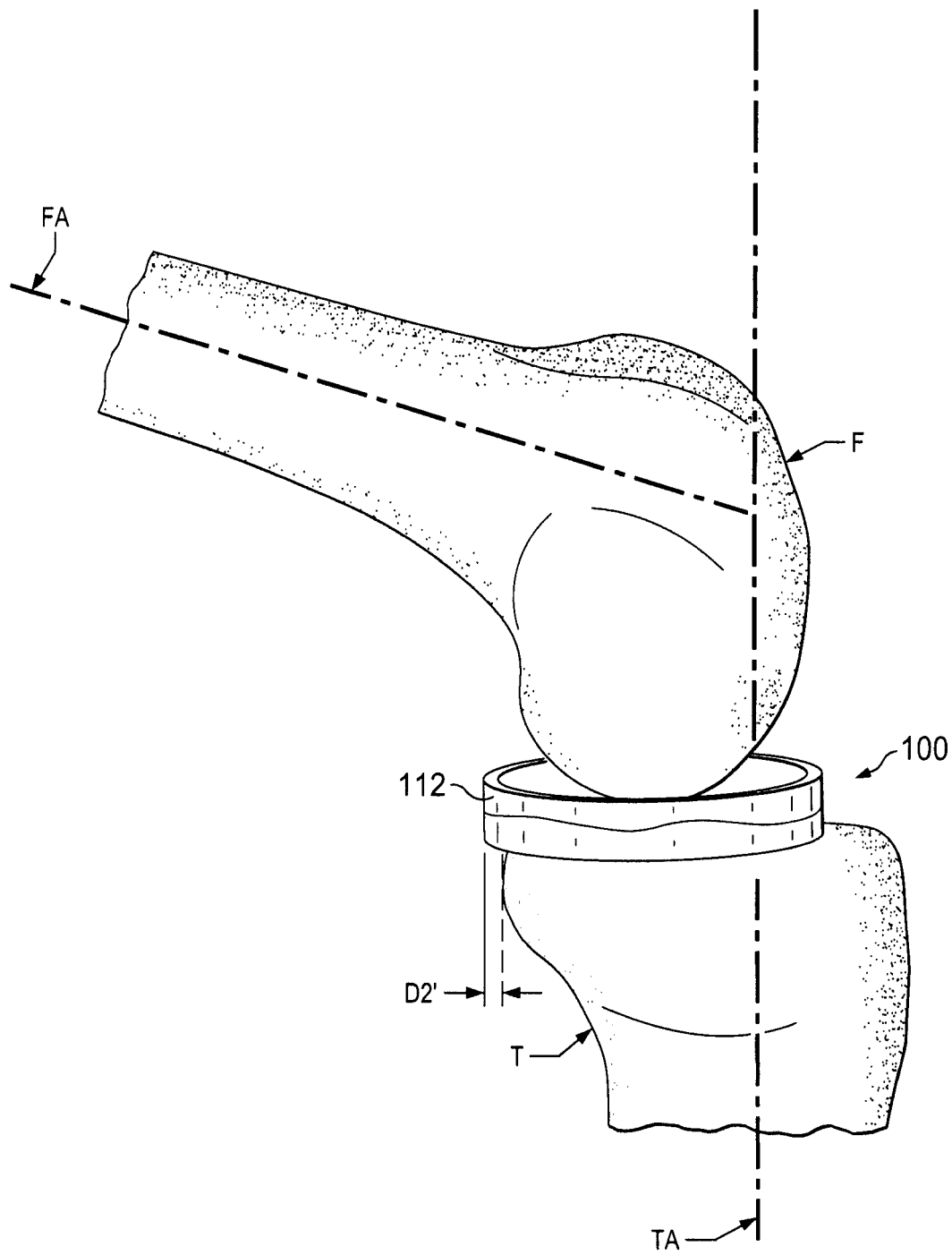
Figure 15C:
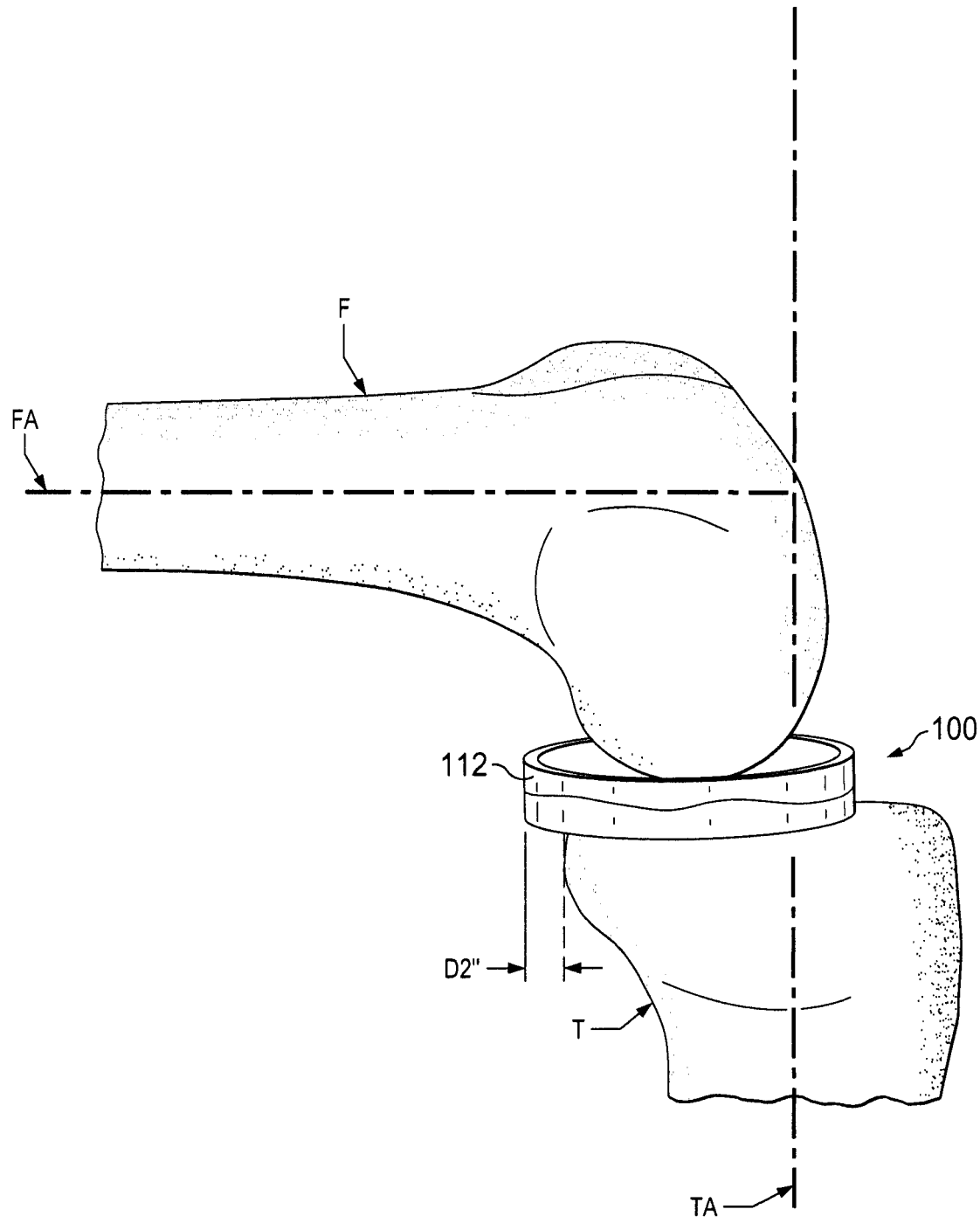
Figure 16A:
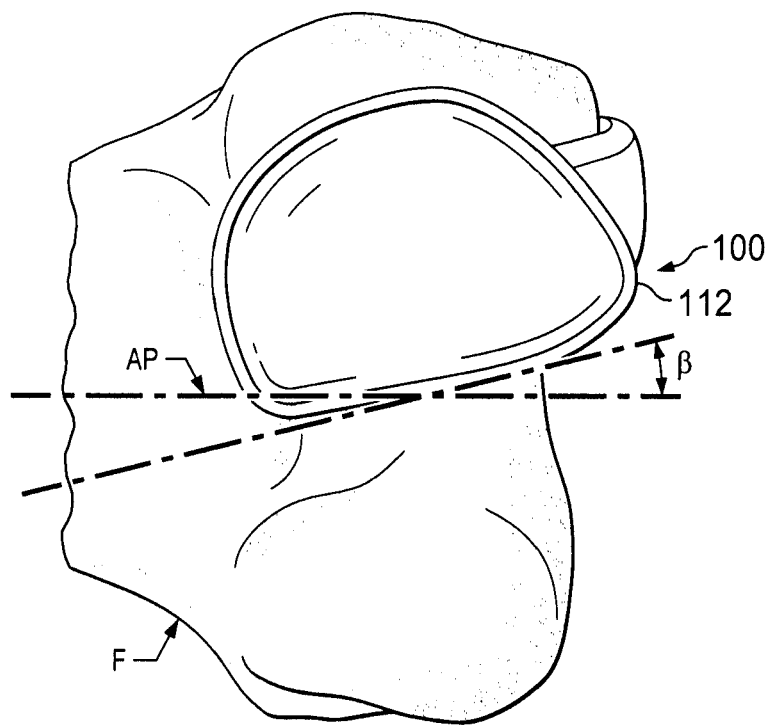
FIGS. 16A, 16B, and 16C illustrate the prosthetic meniscus device with the knee rotating through a series of angles.
Figure 16B:
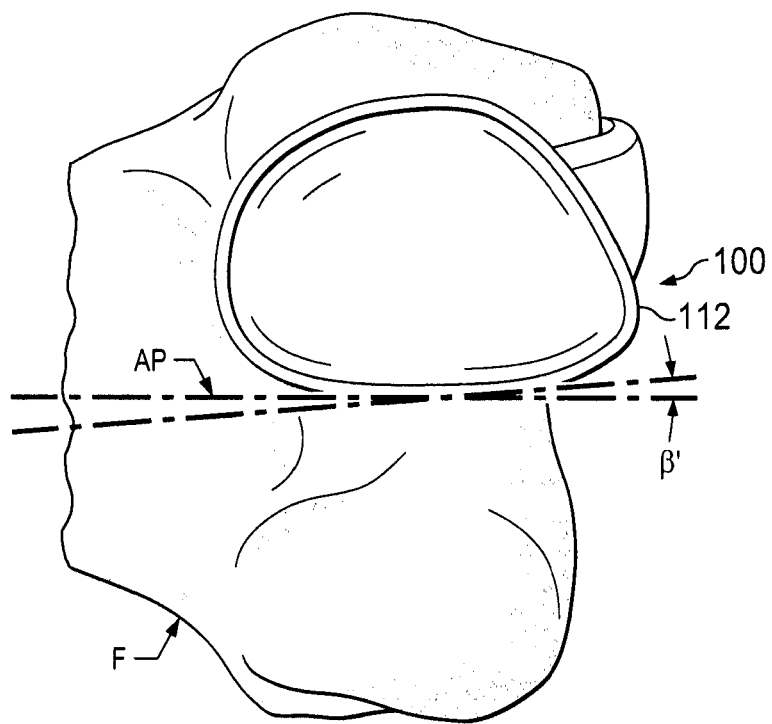

FIGS. 15A, 15B, and 15C show a series of angular positions of the femur F in relation to the tibia T and the correspondent movement of the prosthetic meniscus device 100 in the knee joint. In FIG. 15A, femoral axis FA is substantially aligned with the tibial axis TA. The prosthetic meniscus device 100 is disposed between the tibia T and the femur F. In this initial position, with the axes FA and TA substantially aligned, the outer surface represented by the numerals 112 and 124 of the floating prosthetic meniscus device 100 may be generally aligned with a posterior wall of the joint, referenced again by the reference line 550. FIG. 16A illustrates the view from the tibia in position A and shows the rotational orientation of the prosthetic meniscus device 100 peripheral side surface 112 in relation to the anterior-posterior axis AP. In position A, the angle between the edge of the prosthetic meniscus device 100 and the axis AP is β. FIGS. 15B and 16B illustrate the movement of the prosthetic meniscus device 100 as the femur F is moved to the position of the angle α' between axis FA and axis TA. During such movement, the prosthetic meniscus device 100 displaces in the posterior direction a distance D2'. Additionally, the prosthetic meniscus device 100 has rotated clockwise with respect to axis AP to smaller angle β'. The illustrated relationship is position B. The prosthetic meniscus device 100 has moved longitudinally, rotationally, and/or laterally between positions A and B. Translation of the prosthetic meniscus device 100 along the axis AP can be described as longitudinal movement. Translation of the prosthetic meniscus device 100 along a medial-lateral axis perpendicular to the axis AP can be described as lateral movement.

Figure 16C:
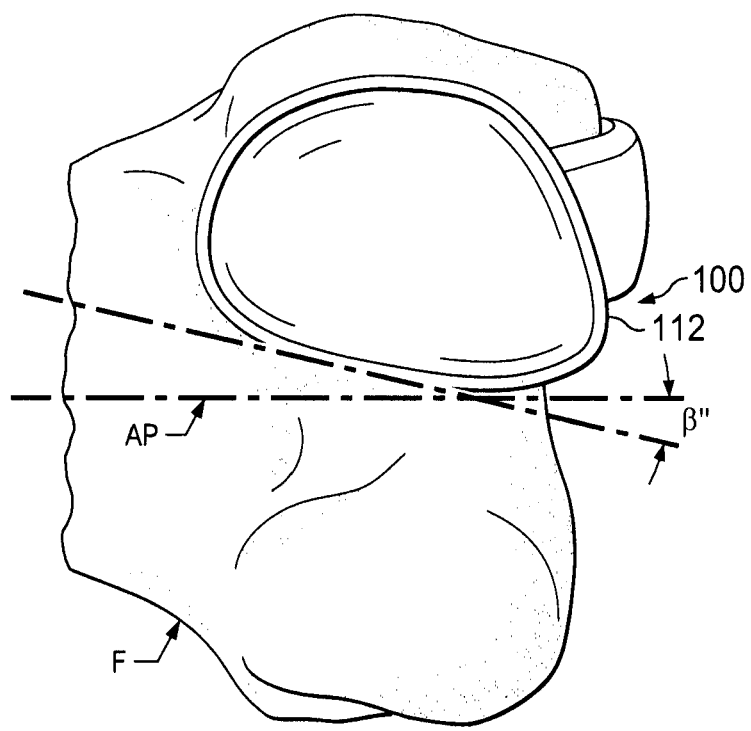

FIG. 15C illustrates that continued rotation of the femur with respect to the tibia to angle α", which is substantially 90 degrees, results in further translation to a distance D2" which is greater than D2'. Additionally, in FIG. 16C the prosthetic meniscus device 100 has rotated clockwise with respect to axis AP to smaller angle β" which now a negative angle in comparison to the AP axis. The illustrated relationship is position C. The prosthetic meniscus device 100 has moved longitudinally, rotationally, and/or laterally between positions B and C, and positions A and C.

While the foregoing are not limiting, the total translation distance can range from 3-20 mm in the anterior to posterior plane, with one embodiment having D2' of 7 mm and D2" of 14 mm. Similarly, the rotational angle can range, without limitation, from 3 to 30 degrees of total angular rotation. With respect to the embodiment shown in FIGS. 16A-16C, β is approximately 10 degrees, β' is approximately 5 degrees, and β" is approximately −5 degrees from the AP line.

As shown above with respect to FIGS. 15A-16C, the prosthetic meniscus device is floating on the natural tibial plateau and translates while simultaneously rotating into the positions shown. In one form, the femoral bearing surface engages the tissue interfacing upper surface on the prosthetic meniscus device 100 to force the device 100 into position A, while a second portion of the femoral bearing surface engages the tissue interfacing upper surface on the prosthetic meniscus device 100 to force the device into position B, while a third portion of the femoral bearing surface engages the tissue interfacing upper surface on the prosthetic meniscus device 100 to force the device into position C.

Figure 17:
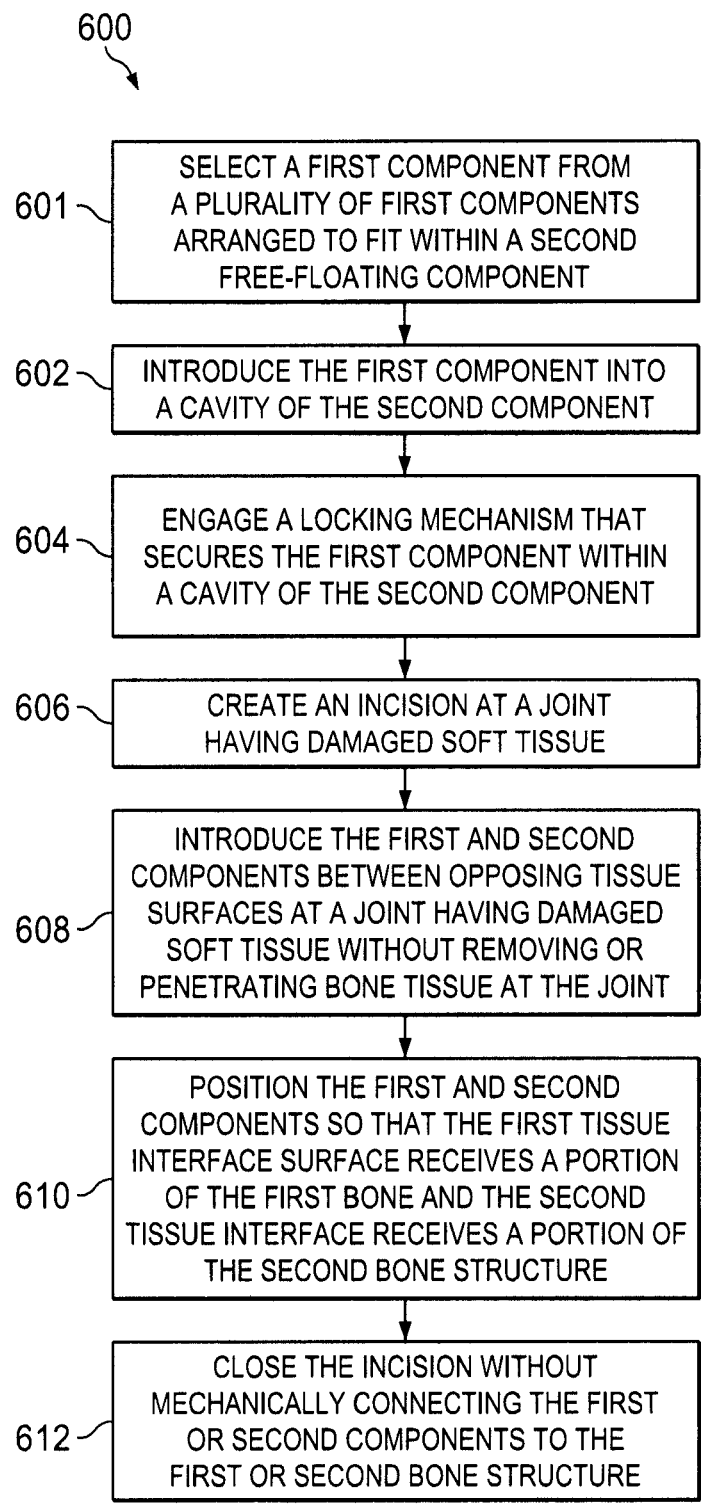
FIG. 17 is a flowchart illustrating an exemplary method of implanting a prosthetic meniscus device in accordance with an exemplary implementation.

FIG. 17 discloses a method 600 of implanting the prosthetic meniscus device according to an exemplary implementation. The method may be performed, for example, with respect to any of the prosthetic meniscus devices described herein. It is understood that additional steps can be provided before, during, and after the steps of method 600, and that some of the steps described can be replaced or eliminated from the method 600.

In some exemplary implementations, the method begins at 602, with a health care provider assembling the prosthetic meniscus device prior to implantation in a patient. Accordingly, at 601, the health care provider may select a first component from a plurality of first components arranged to fit within a second component. The first component may be any of the meniscus components described herein. As described above, in some implementations, a health care provider may be presented with a plurality of meniscus components, with each meniscus component having a particular profile or contour that may match a particular bone structure. In some implementations, the plurality of meniscus components may have similar contours, but may be sized differently to match different sized patients.

At 602, the health care provider may introduce the first component into a cavity of the second component. This may include aligning the noncircular shapes of the meniscus component and the base component and pressing the meniscus component into the cavity of the base component. At 604, the health care provider may engage a locking mechanism that secures the first component within a cavity of the second component. In some implementations, this may include snap fitting the meniscus component into the base component. For example, when the locking mechanism is a groove and a nub, this may include snapping the knob into the groove to secure the meniscus component into the base component. Other locking mechanisms are also contemplated. In some implementations, with the meniscus component secured in the base component, relative movement of the upper and base components may be limited or may be prevented.

At 606, the health care provider may create an incision at a joint of a patient having damaged soft tissue in a manner known in the art. At 608, the health care provider may introduce the first and second components between opposing tissue surfaces at a joint having damaged soft tissue without removing or penetrating bone tissue at the joint. Accordingly, in some implementations, the health care provider does not carve, cut, or introduce screws, fins, or other anchors into the adjacent bone. As such, the prosthetic meniscus device may be free floating within the joint. That is, it may have the ability to move or slide laterally within the joint, and may have the ability to rotate within the joint. Flexion at the joint may cause the prosthetic meniscus device to translate or rotate. Accordingly, the prosthetic meniscus device is devoid of mechanical anchors and is arranged to interface with the natural tibia plateau and the femoral surface.

At 610, the health care provider may position the first and second components so that the first tissue interface surface receives a portion of the first bone the second tissue interface receives a portion of the second bone structure. This may occur when the first tissue-interface surface of the first component and the second tissue interface surface of the second component are shaped to fit contours of the adjacent bone structure. In some implementations, this may include a simple concave surface shaped to receive adjacent bone structure. In other implementations, the first and second components may be particularly shaped to match a particular bone surface. For example, in some implementations the first component is shaped to match the contours of a femoral surface. As such, the first tissue interface surface may receive contours of the femoral bone. Likewise, in some implementations, the second component is shaped to match the contours of a natural tibia plateau. As such, the second tissue interface surface may receive contours of the tibia bone. In other implementations, the tissue interface surfaces may not have specific contours, but may be shaped with concavities or may be relatively planar.

At 612, the health care provider may close the incision without mechanically connecting the first or second components to the first or second bone structure. This may enable the prosthetic meniscus device to free float within the joint.

A variety of materials are suitable for use in making the components of prosthetic devices described herein. In one aspect, the flexible (non-rigid) component forming, such as for example the meniscus component 102 is formed from a material that will yield/deform under normal human loading while the rigid material generally does not deform under normal human loading. An example combination would be a flexible component or layer including a material formed from a polycarbonate-urethane having a hardness value of about 3.0 to 9.0 $N/mm^2$ and the rigid material being formed of stainless steel material, or alternatively, a rigid polyurethane, such as COROTHANE polyurethane 75D, having a hardness in the range of about 45 $N/mm^2$ to 85 $N/mm^2$. Medical grade polyurethane based materials especially suitable for use in the embodiments described include, but are not limited to, isolated or in combination, the following:

Bionate®, manufactured by DSM, a polycarbonate-urethane is among the most extensively tested biomaterials ever developed. Carbonate linkages adjacent to hydrocarbon groups give this family of materials oxidative stability, making these polymers attractive in applications where oxidation is a potential mode of degradation, such as in pacemaker leads, ventricular assist devices, catheters, stents, and many other biomedical devices. Polycarbonate urethanes were the first biomedical polyurethanes promoted for their biostability. Bionate® polycarbonate-urethane is a thermoplastic elastomer formed as the reaction product of a hydroxyl terminated polycarbonate, an aromatic diisocyanate, and a low molecular weight glycol used as a chain extender. The results of extensive testing encompassing Histology, Carcinogenicity, Biostability, and Tripartite Biocompatibility Guidance for Medical Devices verifies the cost effective material's biocompatibility.

Another group of suitable materials are copolymers of silicone with polyurethanes as exemplified by PurSil™, a Silicone Polyether Urethane and CarboSil™, a Silicone Polycarbonate Urethane. Silicones have long been known to be biostable and biocompatible in most implants, and also frequently have the low hardness and low modulus useful for many device applications. Conventional silicone elastomers can have very high ultimate elongations, but only low to moderate tensile strengths. Consequently, the toughness of most biomedical silicone elastomers is not particularly high. Another disadvantage of conventional silicone elastomers in device manufacturing is the need for cross-linking to develop useful properties. Once cross-linked, the resulting thermoset silicone cannot be redissolved or remelted. In contrast, conventional polyurethane elastomers are generally thermoplastic with excellent physical properties. Thermoplastic urethane elastomers (TPUs) combine high elongation and high tensile strength to form tough, albeit fairly high-modulus elastomers. Aromatic polyether TPUs can have an excellent flex life, tensile strength exceeding 5000 psi, and ultimate elongations greater than 700 percent. These materials are often used for continuously flexing, chronic implants such as ventricular-assist devices, intraaortic balloons, and artificial heart components. TPUs can easily be processed by melting or dissolving the polymer to fabricate it into useful shapes.

The prospect of combining the biocompatibility and biostability of conventional silicone elastomers with the processability and toughness of TPUs is an attractive approach to what would appear to be a nearly ideal biomaterial. For instance, in polycarbonate-based polyurethanes, silicone copolymerization has been shown to reduce hydrolytic degradation of the carbonate linkage, whereas in polyether urethanes, the covalently bonded silicone seems to protect the polyether soft segment from oxidative degradation in vivo. DSM synthesized silicone-polyurethane copolymers by combining two previously reported methods: copolymerization of silicone (PSX) together with organic (non-silicone) soft segments into the polymer backbone, and the use of surface-modifying end groups to terminate the copolymer chains.

Other applicable materials include PurSil™ silicone-polyether-urethane and CarboSil™ silicone-polycarbonate-urethane which are true thermoplastic copolymers containing silicone in the soft segment. These high-strength thermoplastic elastomers are prepared through a multi-step bulk synthesis where polydimethylsiloxane (PSX) is incorporated into the polymer soft segment with polytetramethyleneoxide (PTMO) (PurSil) or an aliphatic, hydroxyl-terminated polycarbonate (CarboSil). The hard segment consists of an aromatic diisocyanate, MDI, with low molecular weight glycol chain extender. The copolymer chains are then terminated with silicone (or other) Surface-Modifying End Groups. Aliphatic (AL) versions of these materials, with a hard segment synthesized from an aliphatic diisocyanate, are also available.

Many of these silicone urethanes demonstrate desirable combinations of physical properties. For example, aromatic silicone polyetherurethanes have a higher modulus at a given shore hardness than conventional polyether urethanes—the higher the silicone content, the higher the modulus (see PurSil Properties). Conversely, the aliphatic silicone polyetherurethanes have a very low modulus and a high ultimate elongation typical of silicone homopolymers or even natural rubber (see PurSil AL Properties). These properties make these materials very attractive as high-performance substitutes for conventional cross-linked silicone rubber. In both the PTMO and PC families, some polymers have tensile strengths three to five times higher than conventional silicone biomaterials.

Further examples of suitable materials include Surface Modifying End Groups (SMEs) which are surface-active oligomers covalently bonded to the base polymer during synthesis. SMEs—which include silicone (S), sulfonate (SO), fluorocarbon (F), polyethylene oxide (P), and hydrocarbon (H) groups—control surface chemistry without compromising the bulk properties of the polymer. The result is that key surface properties, such as thromboresistance, biostability, and abrasion resistance, are permanently enhanced without additional post-fabrication treatments or topical coatings. This technology is applied to a wide range of DSM's polymers.

SMEs provide a series of base polymers that can achieve a desired surface chemistry without the use of additives. Polyurethanes prepared according to DSM's development process couple endgroups to the backbone polymer during synthesis via a terminal isocyanate group, not a hard segment. The added mobility of endgroups relative to the backbone facilitates the formation of uniform overlayers by the surface-active end blocks. The use of the surface active endgroups leaves the original polymer backbone intact so the polymer retains strength and processability. The fact that essentially all polymer chains carry the surface-modifying moiety eliminates many of the potential problems associated with additives.

The SME approach also allows the incorporation of mixed endgroups into a single polymer. For example, the combination of hydrophobic and hydrophilic endgroups gives the polymers amphipathic characteristics in which the hydrophobic versus hydrophilic balance may be easily controlled.

Other suitable materials, manufactured by CARDIO-TECH CTE, include ChronoFlex® and Hydrothane™.

The ChronoFlex®, polycarbonate aromatic polyurethanes, family of medical-grade segmented biodurable polyurethane elastomers have been specifically developed by CardioTech International to overcome the in vivo formation of stress-induced microfissures.

HydroThane™, hydrophilic thermoplastic polyurethanes, is a family of super-absorbent, thermoplastic, polyurethane hydrogels ranging in water content from 5 to 25% by weight. HydroThane™ is offered as a clear resin in durometer hardness of 80A and 93 Shore A. The outstanding characteristic of this family of materials is the ability to rapidly absorb water, high tensile strength, and high elongation. The result is a polymer having some lubricious characteristics, as well as being inherently bacterial resistant due to their exceptionally high water content at the surface. HydroThane™ hydrophilic polyurethane resins are thermoplastic hydrogels, and can be extruded or molded by conventional means. Traditional hydrogels on the other hand are thermosets and difficult to process.

Additional suitable materials manufactured by THER-MEDICS include Tecothane® (aromatic polyether-based polyurethane), Carbothane® (aliphatic polycarbonate-based polyurethane), Tecophilic® (high moisture absorption aliphatic polyether-based polyurethane) and Tecoplast® (aromatic polyether-based polyurethane). Tecothane® is a family of aromatic, polyether-based TPU's available over a wide range of durometers, colors, and radiopacifiers. One can expect Tecothane resins to exhibit improved solvent resistance and biostability when compared with Tecoflex resins of equal durometers. Carbothane® is a family of aliphatic, polycarbonate-based TPU's available over a wide range of durometers, colors and radiopacifiers. This type of TPU has been reported to exhibit excellent oxidative stability, a property which may equate to excellent long-term biostability. This family, like Tecoflex, is easy to process and does not yellow upon aging. Tecophilic® is a family of aliphatic, polyether-based TPU's which have been specially formulated to absorb equilibrium water contents of up to 150% of the weight of dry resin.

Additional materials of interest include Tecogel, a new member to the Tecophilic family, a hydrogel that can be formulated to absorb equilibrium water contents between 500% to 2000% of the weight of dry resin, and Tecoplast®, a family of aromatic, polyether-based TPU's formulated to produce rugged injection molded components exhibiting high durometers and heat deflection temperatures.

Additional potentially suitable materials include four families of polyurethanes, named Elast-Eon™, which are available from AorTech Biomaterials.

Elast-Eon™ 1, a Polyhexamethylene oxide (PFMO), aromatic polyurethane, is an improvement on conventional polyurethane in that it has a reduced number of the susceptible chemical groups. Elast-Eon™ 2, a Siloxane based macrodiol, aromatic polyurethane, incorporates siloxane unto the soft segment. Elast-Eon™ 3, a Siloxane based macrodiol, modified hard segment, aromatic polyurethane, is a variation of Elast-Eon™ 2 with further enhanced flexibility due to incorporation of siloxane into the hard segment. Elast-Eon™ 4 is a modified aromatic hard segment polyurethane.

Bayer Corporation also produces candidate materials. Texin 4210 and Texin 4215 are thermoplastic polyurethane/polycarbonate blends for injection molding and extrusion. Texin 5250, 5286 and 5290 are aromatic polyether-based medical grade materials with Shore D hardness of approximately 50, 86, and 90 respectively for injection molding and extrusion.

In some embodiments, the flexible (non-rigid) components of the prosthetic devices are a melt mold composite implant composed of two biocompatible materials: DSM Bionate® Polycarbonate-Urethane (PCU), 80 Shore A, matrix material and ultra high molecular weight polyethylene (UHMWPE) reinforcement material (Dyneema Purity). In some particular embodiments, a component of prosthetic device formed of PCU and reinforced circumferentially with DSM Dyneema® fibers results in a desirable distribution of loads on the underlying articulation surfaces of the components of the prosthetic device.

Although described in the context of a knee system, the prosthetic meniscus devices described herein may be utilized for forming a variety of prosthetic devices. For example, in some instances the composite implants are utilized for knee joints (including meniscus and total knee joints), hip joints (including acetabular cups), shoulder joints, elbow joints, finger joints, ankle joints, and other load and/or non-load receiving prosthetic devices.

It should be appreciated that in some instances the prosthetic meniscus devices described herein may be formed by other processes than those described herein. These manufacturing processes include any suitable manufacturing method. For example, without limitation any of the following manufacturing methods may be utilized: injection molding including inserting inserts; compression molding including inserting inserts; injection-compression molding including inserting inserts; compression molding of prefabricated elements pre-formed by any of the above methods including inserting inserts; spraying including inserting inserts; dipping including inserting inserts; machining from stocks or rods; machining from prefabricated elements including inserting inserts; and/or any of the above methods without inserts. Further, it should be appreciated that in some embodiments the prosthetic devices of the disclosure are formed of medical grade materials other than those specifically identified above. In that regard, in some embodiments the prosthetic devices are formed of any suitable medical grade material.

While the principles of the disclosure have been set forth using the specific embodiments discussed above, no limitations should be implied thereby. Any and all alterations or modifications to the described devices, instruments, and/or methods, as well as any further application of the principles of the disclosure that would be apparent to one skilled in the art are encompassed by the disclosure even if not explicitly discussed herein. It is also recognized that various unforeseen or unanticipated alternatives, modifications, and variations of the disclosure may be subsequently made by those skilled in the art. All such variations, modifications, and improvements that would be apparent to one skilled in the art to which the disclosure relates are encompassed by the following claims.

What is claimed is:

1. A meniscus replacement device for replacing damaged soft tissue at a host knee, the device comprising:

a first component comprising a first tissue-interface surface shaped to free-floatingly interface with a first tissue structure of one of a femur or a tibia in a knee joint having a damaged soft tissue, wherein the first component further comprises a top surface, a bottom surface, and a first outer wall extending between the top surface and the bottom surface; and a second component comprising a second tissue-interface surface shaped to free-floatingly interface with a second tissue structure of the other of the femur or the tibia in the knee joint, the second component having a containment cavity receiving at least a portion of the first component therein to inhibit movement of the first component relative to the second component, wherein the second component further comprises a second outer wall, wherein a size of the first component is less than a size of the second component such that the first outer wall does not extend over the second outer wall.

2. The meniscus replacement device of claim 1, wherein the second tissue-interface surface is shaped to fit contours of a natural tibia plateau.

3. The meniscus replacement device of claim 1, wherein the first tissue-interface surface is shaped to fit contours of a femoral surface.

4. The meniscus replacement device of claim 1, wherein the second outer wall comprises a peripheral side surface that is substantially vertical.

5. The meniscus replacement device of claim 4, wherein the peripheral side surface comprises a radially inwardly facing surface and a radially outwardly facing surface, at least a portion of the surfaces being substantially parallel.

6. The meniscus replacement device of claim 1, wherein the second component comprises a peripheral side surface defining an outer periphery of the meniscus replacement device, the device having a non-circular outer periphery shaped to rotate in a natural meniscus pocket as the host knee bends.

7. The meniscus replacement device of claim 1, wherein a depth of the containment cavity is less than half a width of the second component.

8. The meniscus replacement device of claim 1, wherein the second component comprises a locking structure that secures the first component in the containment cavity.

9. The meniscus replacement device of claim 8, wherein the locking structure comprises a projecting portion that mechanically interferes with removal of the first component from the second component.

10. The meniscus replacement device of claim 8, wherein the first component comprises one of a protrusion and a recess and the second component comprises the other of the protrusion and the recess, the protrusion being receivable into the recess to lock the first component to the second component.

11. The meniscus replacement device of claim 1, wherein the first component further comprises a bone-relief recess formed on the first tissue-interface surface, the bone-relief recess being arranged to prevent load-bearing contact between the first component and a portion of bone structure of the knee.

12. The meniscus replacement device of claim 1, wherein the first outer wall protrudes above the second outer wall.

13. The meniscus replacement device of claim 1,
wherein the first component comprises a radially outwardly facing side surface defining an outer periphery of the first component, and wherein the second component comprises a radially inwardly facing side surface in contact with the radially outwardly facing side surface of the first component.

14. The meniscus replacement device of claim 1,
wherein the first component is formed of a soft material configured for deformation under a typical load of the first tissue structure, and wherein the second component is formed of a relatively rigid material that is more rigid than the soft material and configured to limit the deformation of the soft material of the first component under the typical load.

15. The meniscus replacement device of claim 1, wherein the first outer wall is substantially vertical.

16. The meniscus replacement device of claim 1,
wherein the first component further comprises:
a fiber configured to limit an amount of deformation of the first component under a load; and
a locking structure configured to secure the first component in the containment cavity;
wherein locking structure is proximate to the fiber.

17. The meniscus replacement device of claim 16,
wherein the fiber is arranged vertically between the top surface and the bottom surface of the first component, and wherein the locking structure comprises a projection extending horizontally from the first outer wall in a direction perpendicular to the fiber.

18. The meniscus replacement device of claim 1, wherein the containment cavity completely surrounds a perimeter of the first component such that the movement of the first component is inhibited in all directions.

19. A disc-shaped joint replacement device for replacing damaged soft tissue at a host joint, the device comprising:
a first component comprising a first tissue-interface surface shaped to free-floatingly interface with a first tissue structure of the joint, the first tissue-interface surface comprising a concave shape arranged to receive the first tissue structure, wherein the first component further comprises a top surface, a bottom surface, and a first outer wall extending between the top surface and the bottom surface; and a second component comprising a second tissue-interface surface shaped to free-floatingly interface with a second tissue structure of the joint opposing the first tissue structure, the second component having a containment cavity receiving at least a portion of the first component therein, wherein the second component further comprises a second outer wall, wherein the first and second components together have a disc-shape, and wherein a size of the first component is less than a size of the second component such that the first outer wall does not extend over the second outer wall.

20. The joint replacement device of claim 19, wherein the second tissue-interface surface is shaped to fit contours of a natural tibia plateau.

21. The joint replacement device of claim 19, wherein the first tissue-interface surface is shaped to fit contours of a femoral surface.

22. The joint replacement device of claim 19, wherein the second outer wall is substantially vertical.

23. The joint replacement device of claim 19, wherein the second outer wall comprises a radially inwardly facing surface and a radially outwardly facing surface, at least a portion of the surfaces being substantially parallel.

24. The joint replacement device of claim 19, wherein the first component is formed of a relatively more soft first material and the second component is formed of a relatively less soft second material that is shaped to receive and limit radial expansion of the first material.

25. The joint replacement device of claim 19, wherein the second outer wall defines an outer periphery of the meniscus replacement device, the device having a non-circular outer periphery shaped to rotate in a natural meniscus pocket when the host knee bends.

26. The joint replacement device of claim 19, wherein the depth of the containment cavity is less than half the width of the second component.

27. The joint replacement device of claim 19,
  wherein the first component is formed of a relatively more soft material configured to partially deform under load of the first tissue structure of the joint,
  wherein the second component is formed of a relatively more rigid material and configured to limit radial expansion of the first component under the load.

28. The meniscus replacement device of claim 27, wherein the soft material of the first component is configured to radially expand under the typical load and the relatively rigid material of the second component configured to limit the radial expansion of the soft material of the first component under the typical load.

* * * * *